(12) United States Patent
Ohshima et al.

(10) Patent No.: US 9,278,905 B2
(45) Date of Patent: Mar. 8, 2016

(54) PRODUCTION METHOD FOR COMPOUND COMPRISING AMINO GROUP AND/OR HYDROXYL GROUP

(71) Applicants: Takashi Ohshima, Fukuoka (JP); Hiroyuki Morimoto, Fukuoka (JP); Yuhei Shimizu, Fukuoka (JP)

(72) Inventors: Takashi Ohshima, Fukuoka (JP); Hiroyuki Morimoto, Fukuoka (JP); Yuhei Shimizu, Fukuoka (JP)

(73) Assignee: Kyushu University, National University Corporation, Fukuoka (JP)

( * ) Notice: Subject to any disclaimer, the term of this patent is extended or adjusted under 35 U.S.C. 154(b) by 0 days.

(21) Appl. No.: 14/382,455

(22) PCT Filed: Mar. 4, 2013

(86) PCT No.: PCT/JP2013/055845
§ 371 (c)(1),
(2) Date: Sep. 2, 2014

(87) PCT Pub. No.: WO2013/129682
PCT Pub. Date: Sep. 6, 2013

(65) Prior Publication Data
US 2015/0105559 A1 Apr. 16, 2015

(30) Foreign Application Priority Data

Mar. 2, 2012 (JP) .................................. 2012-046588
Dec. 3, 2012 (JP) .................................. 2012-264569

(51) Int. Cl.
| | | |
|---|---|---|
| *C07C 211/00* | (2006.01) |
| *C07C 209/62* | (2006.01) |
| *C07D 217/02* | (2006.01) |
| *C07B 41/02* | (2006.01) |
| *C07B 43/04* | (2006.01) |
| *C07B 51/00* | (2006.01) |
| *C07C 213/02* | (2006.01) |
| *C07C 227/06* | (2006.01) |
| *C07D 209/16* | (2006.01) |
| *C07F 7/18* | (2006.01) |
| *C07C 41/26* | (2006.01) |
| *C07C 29/00* | (2006.01) |
| *C07C 41/18* | (2006.01) |
| *C07C 227/04* | (2006.01) |
| *C07D 209/08* | (2006.01) |
| *C07D 309/12* | (2006.01) |
| *C07D 317/28* | (2006.01) |

(52) U.S. Cl.
CPC .............. *C07C 209/62* (2013.01); *C07B 41/02* (2013.01); *C07B 43/04* (2013.01); *C07B 51/00* (2013.01); *C07C 29/00* (2013.01); *C07C 41/18* (2013.01); *C07C 41/26* (2013.01); *C07C 213/02* (2013.01); *C07C 227/04* (2013.01); *C07C 227/06* (2013.01); *C07D 209/08* (2013.01); *C07D 209/16* (2013.01); *C07D 217/02* (2013.01); *C07D 309/12* (2013.01); *C07D 317/28* (2013.01); *C07F 7/1852* (2013.01); *C07F 7/1892* (2013.01); *C07C 2103/74* (2013.01)

(58) Field of Classification Search
CPC ...................................................... C07C 209/62
USPC ................................................. 564/368, 371
See application file for complete search history.

(56) References Cited

U.S. PATENT DOCUMENTS 4,507,433 A 3/1985 Miller et al.

FOREIGN PATENT DOCUMENTS

| CN | 101463072 A | 6/2009 |
| JP | 2007-246400 A | 9/2007 |

OTHER PUBLICATIONS

Shimizu et al. Angew. Chem. Int. Ed. 2012, 51, 8564-8567.*
Cros et al., "*N*-Tetrachlorophthaloyl (TCP) Protection for Solid-Phase Peptide Synthesis", European Journal of Organic Chemistry, No. 17, p. 3633-3642 (2004) (English Text).
Ishido et al., "Regioselective *O*-Deacylation of Fully Acylated Glycosides and 1,2-*O*-Isoproylidenealdofuranose Derivatives With Hydrazine Hydrate", Carbohydrate Research, vol. 97, No. 1, p. 51-79 (1981) (English Text).
Barton et al., "Nouvelle Approche Vers Le Squelette De L'Acide Lysergique A Partir Du β-Naphtol", Bulletin de la Societe Chimique De France, No. 4, p. 681-687 (1988) (English Abstract).
Shimizu et al., "Microwave-Assisted Deacylation of Unactivated Amides Using Ammonium-Salt-Accelerated Transamidation", Angewandte Chemie, International Edition, vol. 51, No. 34, p. 8564-8567 (2012) (English Text).
Espino et al., "A Rh-Catalyzed C—H Insertion Reaction for the Oxidative Conversion of Carbamates to Oxazolidinones", Angewandte Chemie, International Edition, vol. 40, No. 3, p. 598-600 (2001) (English Text).

(Continued)

*Primary Examiner* — Nizal Chandrakumar
(74) *Attorney, Agent, or Firm* — Fay Sharpe LLP

(57) ABSTRACT

Disclosed is a method for producing a compound having an amino group and/or a hydroxyl group from a substrate compound having an atomic group containing CO or CS by eliminating such atomic group. The substrate compound, having an atomic group containing CO or CS (for example, an amide, a carbamate, or the like), is allowed to react with a compound expressed by formula (I) below, at a temperature of 120° C. or lower, preferably in the presence of an ammonium salt, to eliminate such atomic group containing CO or CS. In formula (I) A may not be present, and in a case where A is present, A represents an alkyl group having 1 to 6 carbon atoms.

$$H_2N-A-NH_2 \qquad (I).$$

14 Claims, No Drawings

(56) References Cited

OTHER PUBLICATIONS

Jiang et al., "Sequential Allylic C—H Amination/Vinylic C—H Arylation: A Strategy for Unnatural Amino Acid Synthesis From α-Olefins", Organic Letters, vol. 14, No. 6, p. 1386-1389, (2012) (English Text).

International Search Report of International Application No. PCT/JP2013/05585 dated Jun. 11, 2013, 7 pages.

Geiger et al., "Abspaltung der N-Formylgruppe durch Hydrazinacetat, Hydrazinderivate und Hydroxylamin" ("Cleavage of the N-Formylgruppe by hydrazine acetate, hydrazine and hydroxylamine"), Chemische Berichte, vol. 101, No. 10, p. 3386-3391 (1968) (English Abstract included).

Excoffier et al., "Coupure sélective par l'hydrazine des groupements acetyls anoméres de résidus glycosyles acétylés" ("Use of hydrazine for selective clipping of anomeric acetyl groups of acetyl glycosyl residues"), Carbohydrate Research, vol. 39, No. 2, p. 368-373 (1975) (English translation included).

Morin, et al., "Reductive Cleavage of Aryl $O$-Carbamates to Phenols by the Schwartz Reagent. Expedient Link to the Directed *Ortho* Metalation Strategy," Organic Letters, vol. 15, No. 16, pp. 4102-4105 (2013).

Didier, et al., "Chemo-Enzymatic Synthesis of 1, 2- and 1, 3 Amino-Alcohols and Their Use in the Enantioselective Reduction of Acetophenone and Anti-Acetophenone Oxime Methyl Ether with Borane," Tetrahedron, vol. 47, No. 27, pp. 4941-4958 (1998).

Balaraman, et al., "Unprecedented Catalytic Hydrogenation of Urea Derivatives to Amines and Methanol," Angew. Chem. Int. Ed., vol. 50, pp. 11702-11705 (2011).

Balaraman, et al., "Efficient Hydrogenation of Organic Carbonates, Carbamates and Formates Indicates Alternative Routes to Methanol Based on $CO_2$ and CO," Nature Chemistry, vol. 3, pp. 609-614 (2011).

\* cited by examiner

PRODUCTION METHOD FOR COMPOUND COMPRISING AMINO GROUP AND/OR HYDROXYL GROUP

TECHNICAL FIELD

The present invention relates to a novel method for producing a compound having an amino group and/or a hydroxyl group by eliminating an acyl group or carbonyl group (including a thiocarbonyl group) under a mild condition.

BACKGROUND ART

Amino group (—$NH_2$) or hydroxyl group (—OH) is one of the most important functional groups and contained in many useful compounds including pharmaceutical products and intermediates for synthesizing such products.

An amino group reacts very easily with a variety of reagents and it is therefore necessary to have the high reactivity of the amino group masked by a protecting group, followed by deprotection or deblocking at the final stage of synthesis so as to restore the original amino group. A versatile protecting group for an amino group is carbamate-based protecting group such as Boc group or Fmoc group, both of which have become indispensable protecting groups for peptide synthesis.

Acyl group, typified by acetyl group, is widely used as a protecting group for hydroxyl group, but its use as a protecting group for amino group is very limited. This is because an amide bond is thermodynamically very stable as compared with an ester bond, and therefore the deprotection for an acyl group needs to be carried out under strong acidic conditions (e.g. using hydrochloric acid or sulfuric acid) or basic conditions (e.g. using sodium hydroxide) so as to promote a hydrolysis reaction, generally at a high temperature exceeding 100° C. Thus, there is a restriction that the reaction can be applied only to stable substrates having no functionalized groups and hence being able to resist under such severe conditions.

On the other hand, an acyl group is a preferable protecting group in terms of chemical process, as compared with the abovementioned carbamate group, because it can coexist with various types of reactants and can be introduced inexpensively. The products of asymmetric hydrogenation reaction (which products are widely used in the synthesis of optically active α-amino acids) are almost completely limited to N-acyl amino acid derivatives. Consequently, N-deacylation reaction under a mild condition would make it possible to greatly improve the efficiency of the current synthesis process for medical products. However, there have been hitherto developed no methods other than the enzymic method, by which amide bonds can be hydrolyzed for deacylation under a mild condition.

As compounds having CO-containing atomic groups like amides, there are known cyclic carbamates, chain carbamates, cyclic carbonates, chain carbonates, cyclic ureas, chain ureas and the like, all of which contain a carbonyl group. These compounds are also important for obtaining useful compounds having an amino group and/or a hydroxyl group and other purposes. For example, cyclic carbamates are utilized in the synthesis and protection of amino alcohol and have recently attracted attention as synthetic intermediates obtained by activation of the C—H bond [e.g. Angew. Chem., Int. Ed. 2001, 40, 598 (Non-patent reference No. 1): Org. Lett. 2012, 14, 1386 (Non-patent reference No. 2)]. However, the decarbonylation of a cyclic carbamate generally requires a strong basic condition using barium hydroxide or lithium hydroxide and therefore has room for improvement in substrate versatility.

PRIOR ART

Non-Patent References

Non-patent Reference No. 1: Angew. Chem., Int. Ed. 2001, 40, 598

Non-patent Reference No. 2: Org. Lett. 2012, 14, 1386

SUMMARY OF THE INVENTION

Problems to be Solved by the Invention

The object of the present invention is to provide a new technique for producing useful products having an amino group and/or a hydroxyl group from a variety of substrate compounds having an atomic group containing acyl group or carbonyl group, by eliminating the atomic group containing the acyl group and or carbonyl group under a mild condition.

Means for Solving the Problems

After extensive studies, the present inventors found that utilization of specific compounds having $NH_2$ groups enable the elimination of acyl group or carbonyl group, under a mild condition, from a variety of substrate compounds having acyl group, carbonyl group or thiocarbonyl group.

Thus, the present invention provides a method for producing a compound having an amino group and/or a hydroxyl group from a substrate compound having an atomic group containing CX, where X represents an oxygen atom or a sulfur atom, which comprises allowing said substrate compound to react with a compound expressed by formula (I) below under a neutral condition at a temperature of 120° C. or lower to eliminate said atomic group containing CX from said substrate compound:

$$H_2N\text{-}A\text{-}NH_2 \qquad (I)$$

wherein A may not be present and in a case where A is not present, formula (I) is hydrazine, and in a case where A is present, A represents an alkyl group having 1 to 6 carbon atoms and the formula (I) represents an alkylamine having said alkyl group in which one or two of the carbon atoms may be substituted with nitrogen atom(s).

The abovementioned reaction in the method according to the present invention is most preferably carried out in the presence of an ammonium salt.

Advantageous Effects of the Invention

The method according to the present invention for producing the compounds having an amino acid and/or a hydroxyl group enjoys the following advantageous effects and provides a very practical technique for the purpose of obtaining a variety of functionalized or useful compounds including medical supplies and other purposes: (1) The reaction condition is mild (under neutral condition at a reaction temperature of 120° C. or lower, generally 50-90° C.) and thus the method can be applied to a substrate compound having various coexistent functional groups in addition to acyl group, carbonyl group or thiocarbonyl group, (2) The compounds expressed by the formula (I) and the ammonium compound used are low-priced reagents, and (3) The reaction can proceed even in the absence of solvent.

MODE FOR CARRYING OUT THE INVENTION

The compound of the abovementioned formula (I) used in the method of the present invention is considered to be the one that serves as a nucleophilic reagent.

Of the compounds expressed by the formula (I), the compound in which A is not present, i.e. hydrazine, is particularly suitable for producing a compound having an amino group from an amide as the substrate compound wherein the atomic group including CX is acyl group (that is, CX is CO) and the acyl group is eliminated to produce the compound having the amino group. The reaction can proceed efficiently even without microwave irradiation as described later. Hydrazine is usually used as a monohydrate. By contrast, decarbonylation or dethiocarbonylation reaction using hydrazine will generally result in a low yield of the target compounds.

In the formula (I), in case that A is present, A represents an alkyl group having 1 to 6 carbon atoms and thus the formula (I) represents an alkylamine having said alkyl group, wherein one or two of the carbon atoms may be substituted with nitrogen atom(s). Suitable alkylamines for use in the present invention are exemplified by, but not limited to, the ones expressed by the following formulae:

[C.F. 1]

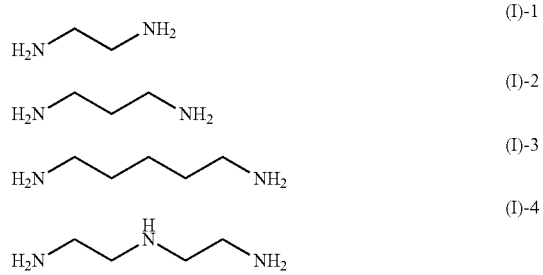

Of these compounds, the particularly preferable alkylamine is ethylenediamine expressed by the formula (I)-1 in terms of price and availability in addition to reactivity.

The abovementioned alkylamines are particularly suitable for the production of a compound having an amino group from an amide as the substrate compound, wherein the atomic group containing CX is N-acyl group (i.e. CX is CO), by eliminating the acyl group.

These alkylamines are also suitable for the production of a compound having an amino group and/or a hydroxyl group from a cyclic carbamate, a chain carbamate, a cyclic carbonate, a chain carbonate, a cyclic urea or a chain urea as the substrate compound, wherein the atomic group containing CX is a carbonyl group (i.e. CX is CO), by eliminating the carbonyl group.

Furthermore, the abovementioned alkylamines are found to be applicable to the production of a compound having an amino group and/or a hydroxyl group from a cyclic thiocarbamate, a chain thiocarbamate, a cyclic thiocarbonate, chain thiocarbonate, a cyclic thiourea or chain thiourea, wherein the atomic group containing CX is a thiocarbonyl group (i.e. CX is CS), by eliminating the thiocarbonyl group.

The reactant expressed by the formula (I) may be used generally in the ratio of 1.0 to 10.0 equivalents (by molar equivalent) to the substrate compound as the starting material. For example, the alkylamine may preferably be used in the ratio of 4.0 equivalents to the substrate compound, and hydrazine may preferably be used in the ratio of 10.0 equivalents to the substrate compound.

The method of the present invention is most preferably carried out in the presence of an ammonium salt. The ammonium salt serves as a catalyst. While either an inorganic ammonium salt or an organic ammonium salt may be used in principle, inorganic ammonium salts are preferably used, of which ammonium halides are particularly preferred in consideration of both reactivity and prices and thus, $NH_4Cl$ (ammonium chloride), $NH_4Br$ (ammonium bromide), $NH_4I$ (ammonium iodide) or a mixture thereof may preferably used. Such ammonium halide may be used generally in the ratio of 0.1 to 5.0 equivalents (by molar equivalent) to the substrate compound as the starting material, with product yield increasing as said ratio increases.

The method of the present invention can be carried out under a mild reaction condition, generally neutral condition at a temperature of 120° C. or lower, usually at 50 to 90° C. While the reaction time is not limited, it is generally for 3 to 50 hours.

Another characteristic feature of the method of the present invention for producing compounds having an amino group and/or hydroxyl group resides in that it can be carried out even in the absence of any solvent. The reaction may proceed in the presence of a hydrocarbon-type solvent such as toluene or alcohol-type solvent such as ethanol, but the reaction will proceed more efficiently without solvent(s). It is further to be noted that the reaction time is significantly shortened by microwave irradiation.

The reaction equation by which the method of the present invention proceeds can be expressed by the formula (II) below, for example, in the case where the substrate compound is an amide carrying an acyl group (N-acyl group) and the acyl group is eliminated from the amide:

[C.F. 2]

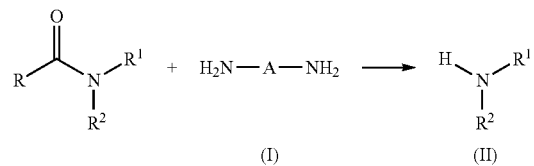

It is believed that the reactant of the formula (I) has a dual role: It not only serves to activate the amide bond due to the hydrogen bonding but also serves as a nucleophilic reagent. The present invention thus provides a method by which an amide is utilized for producing the corresponding amino group-containing compound under a very mild condition.

In addition, the method of the present invention can be applied to a variety of compounds containing carbonyl group in the atomic group, such as cyclic or chain carbamates (which may be expressed by a general formula $R_2N$—CO—OR), cyclic or chain carbonates (which may be expressed by a general formula RO—CO—OR), and cyclic or chain urea (which may be expressed by a general formula $R_2N$—CO—$NR_2$), and further to cyclic or chain thiocarbamates and cyclic or chain thioureas, which contain a thiocarbonyl group (CS) in place of a carbonyl group (CO), so as to remove such compounds from the carbonyl group or the thiocarbonyl group to produce a corresponding compound having an amino group and/or hydroxyl group.

For example, in a case where the compound containing a carbonyl group is a chain urethane, the reaction equation according to the present invention can be expressed by the following equation (III). The reaction will proceed efficiently under a mild condition just as in the abovementioned deacylation reaction.
[C.F. 3]

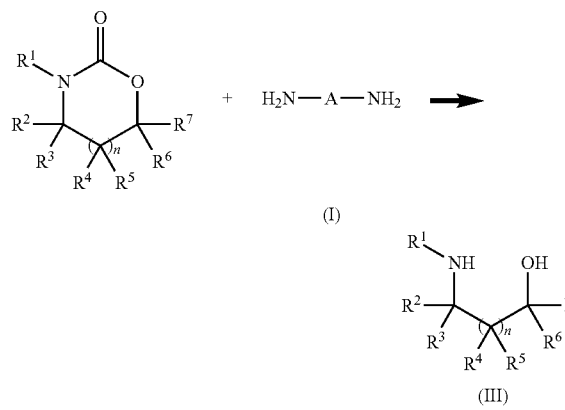

While the features of the present invention will be elucidated in a more concrete manner by the following working examples, the present invention is not restricted by these examples.

Example 1

Studies on Optimum Reaction Conditions

The optimum reaction conditions were studied with respect to the deacylation of amides as an example.
1.1 Studies on Reactants
As shown by the reaction equation given below, to 74.6 mg (0.50 mmol) of N-benzylacetamide as an amide was added 4.0 equivalents of one of the amine listed in Table 1 below as the reactant, in the presence of 1.0 equivalent of ammonium chloride, for the reaction at 80° C. (in oil bath) under heating with stirring.
[C.F. 4]

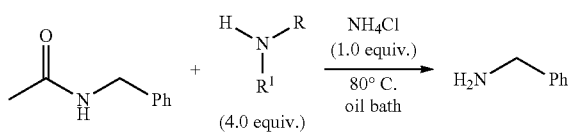

TABLE 1

| Run No. | Amine | Reaction Time (hr) | Yield (%)[a] |
|---|---|---|---|
| 1 | CH$_3$(CH$_2$)$_4$NH$_2$ | 20 | 8 |
| 2 | H$_2$N-CH$_2$CH$_2$-NH$_2$ | 18 | 31 |
| 3 | CH$_3$NH-CH$_2$CH$_2$-NH$_2$ | 18 | 13 |
| 4 | CH$_3$NH-CH$_2$CH$_2$-NHCH$_3$ | 18 | 0 |

TABLE 1-continued

| Run No. | Amine | Reaction Time (hr) | Yield (%)[a] |
|---|---|---|---|
| 5 | (CH$_3$)$_2$N-CH$_2$CH$_2$-NH$_2$ | 18 | 16 |
| 6 | (CH$_3$)$_2$N-CH$_2$CH$_2$-N(CH$_3$)$_2$ | 18 | 0 |
| 7 | CH$_3$CH(NH$_2$)CH$_2$NH$_2$ | 18 | 12 |
| 8 | cis-1,2-diaminocyclohexane | 18 | 0 |
| 9 | trans-1,2-diaminocyclohexane | 18 | 0 |
| 10 | H$_2$N(CH$_2$)$_3$NH$_2$ | 18 | 12 |
| 11 | H$_2$N(CH$_2$)$_4$NH$_2$ | 18 | 7.0 |
| 12 | H$_2$N(CH$_2$)$_5$NH$_2$ | 18 | 11 |
| 13 | H$_2$N(CH$_2$)$_6$NH$_2$ | 18 | 4.1 |

[a]Yield was determined by $^1$H NMR analysis.

Several types of diamines were studied, and the best yield was obtained with respect to ethylenediamine.
1.2 Studies on the Amounts of Ethylene Diamine
As shown by the reaction equation given below, to 74.6 mg (0.50 mmol) of N-benzylacetamide was added varying amounts (equivalents) of ethylenediamine as listed in Table 2 below, in the presence of 1.0 equivalent of ammonium chloride, for the reaction at 80° C. (in oil bath) under heating with stirring.
[C.F. 5]

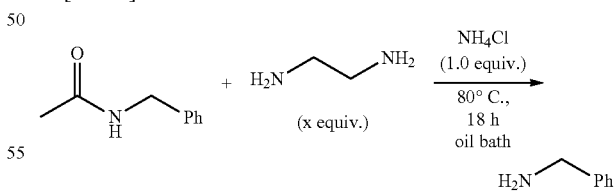

TABLE 2

| Run No. | xEquivalents | Yield (%)[a] |
|---|---|---|
| 1 | 4.0 | 31 |
| 2 | 2.0 | 18 |
| 3 | 3.0 | 32 |
| 4 | 8.0 | 17 |

[a]Yield was determined by $^1$H NMR analysis

Almost the same results were obtained with respect to the Run No. 1 and 3.

1.3 Studies on Solvents

As shown by the reaction equation below, to 74.6 mg (0.50 mmol) of B-benzylacetamide was added 500 μL of one of the solvents listed in the following table and 133 μL (2.0 mmol) of ethylenediamine, in the presence of 1.0 equivalent of ammonium chloride, followed by heating in oil bath with stirring.

[C.F. 3]

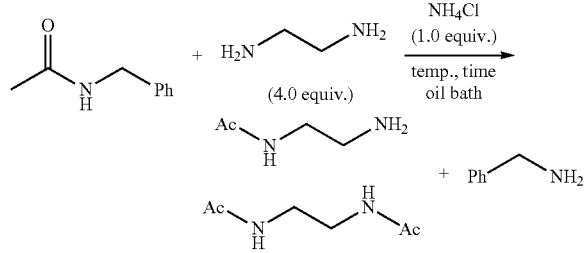

TABLE 3

| Run. No. | Solvent | Reactant | Equiv. of Reactant | Reaction Temperature (° C.) | Reaction Time (hr.) | Yield (%)[a] |
|---|---|---|---|---|---|---|
| 1 | (No Solvent) | NH$_4$Cl | 1.0 | 80 | 18 | 31 |
| 2 | Water | NH$_4$Cl | 1.0 | 80 | 20 | 0 |
| 3 | EtOH | NH$_4$Cl | 1.0 | 80 | 20 | 11 |
| 4 | toluene | NH$_4$Cl | 1.0 | 80 | 20 | 12 |
| 5 | cyclopenthyl methyl ether | NH$_4$Cl | 1.0 | 80 | 20 | 0 |
| 6 | Cl(CH$_2$)$_2$Cl | NH$_4$Cl | 1.0 | 80 | 20 | 0 |
| 7 | DMSO | NH$_4$Cl | 1.0 | 80 | 20 | 0 |

[a]Yield was determined by $^1$H NMR analysis.

As shown in Table 3, the best result was obtained under neat condition (in the absence of solvent).

1.4 Studies on Ammonium Salts

As shown by the reaction equation below, to 74.6 mg (0.50 mmol) of N-benzylacetamide was added 133 μL (2.0 mmol) of ethylenediamine, in the presence of one of the ammonium salts listed in the table below, followed by heating in oil bath with stirring.

[C.F. 7]

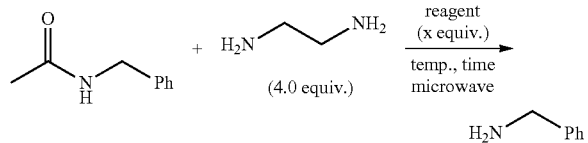

TABLE 4

| Run No. | Reactant | Eequiv. of Reactant | Reaction Temperature (° C.) | Reaction Time (hr) | Yield (%)[a] |
|---|---|---|---|---|---|
| 1 | NH$_4$Cl | 1.0 | 100 | 18 | 81 |
| 2 | NH$_4$Cl | 1.0 | 80 | 18 | 34 |
| 3 | H$_2$N(CH$_2$)$_2$NH$_2$•2HCl | 1.0 | 80-90 | 18 | 41 |
| 4 | NH$_4$Br | 1.0 | 80 | 20 | 36 |
| 5 | NH$_4$I | 1.0 | 80 | 18 | 40 |
| 6 | NH$_4$HCO$_3$ | 1.0 | 80 | 20 | 8.7 |
| 7 | NH$_4$HCO$_2$ | 1.0 | 80 | 20 | 15 |
| 8 | NH$_4$CH$_3$CO$_2$ | 1.0 | 80 | 20 | 25 |
| 9 | (NH$_4$)$_2$HPO$_4$ | 0.5 | 80 | 20 | 0 |

[a] Yield was determined by $^1$H NMR analysis.

Several types of ammonium salts were studied for reactivity, and it was found that excellent results were obtained with respect to ammonium halides, for which the descending order of reactivity was NH$_4$I>NH$_4$Br>NH$_4$Cl.

1.5 Studies on the Amount of Ammonium Salt Under Microwave Irradiation

As shown by the reaction equation below, to 149.2 mg (1.0 mmol) of N-benzylacetamide was added 266 μL (4.0 mmol) of ethylenediamine, in the presence of one of the ammonium salts listed in Table 5 below, followed by the reaction under microwave irradiation.

[C.F. 8]

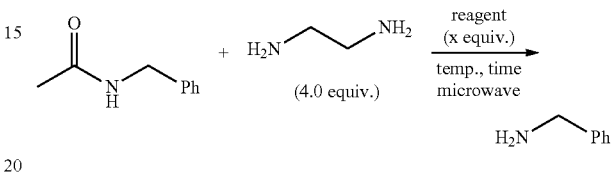

TABLE 5

| Run No. | Reactant | Equiv. of Reactant | Reaction Temperature (° C.) | Reaction Time (hr.) | Yield (%)[a] |
|---|---|---|---|---|---|
| 1 | NH$_4$Cl | 1.0 | 70 | 3 | 47 |
| 2 | NH$_4$Cl | 2.0 | 70 | 3 | 66 |
| 3 | NH$_4$Br | 1.0 | 70 | 3 | 65 |
| 4 | NH$_4$Br | 2.0 | 70 | 3 | 72 |
| 5 | NH$_4$I | 1.0 | 70 | 3 | 67 |
| 6 | NH$_4$I | 2.0 | 70 | 3 | 78 |
| 7 | NH$_4$Br | 2.0 | 60 | 15 | 73 |

[a]Yield was determined by $^1$H NMR analysis.

The yield increased with increasing amount (equivalents) of ammonium salt. The descending order of reactivity was NH$_4$I>NH$_4$Br>NH$_4$Cl. As indicated by Run No. 7, extended reaction time allowed the reaction to proceed sufficiently even at 60° C.

Example 2

Deacylation Using Ethylene Diamine (No. 1)

As shown by the reaction equation below, deacylation reaction was carried out with different types of amides as listed in Table 6-1 and Table 6-2. To 1.0 mmol of each amide and 1.0 equiv. of ammonium bromide was added 266 μL (4.0 equiv.) of ethylenediamine, followed by the reaction under microwave irradiation. The respective reaction conditions and product identification data ($^1$H NMR data and $^{13}$C NMR data) are set out later together with the reaction equations.

[C.F. 9]

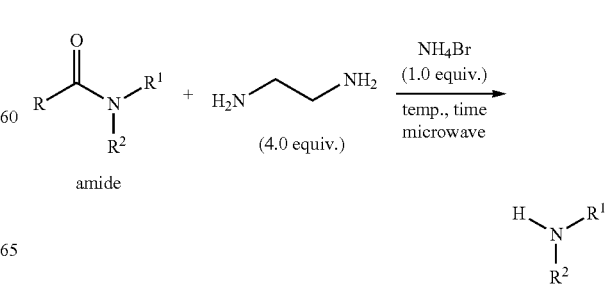

TABLE 6-1
| Entry No. | Amide | Reaction Temperature (° C.) | Reaction Time (hr.) | Yield (%)[a] |
|---|---|---|---|---|
| 1 |  | 80<br>80<br>90 | 5<br>10<br>10 | 90<br>79[b,c]<br>90[b,c] |
| 2 | 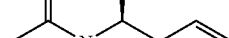 | 80 | 10 | 93 |
| 3 |  | 100 | 10 | 88 |
| 4 |  | 80 | 5 | 89 |
| 5 |  | 80 | 5 | 81(89[c]) |
| 6 |  | 80 | 5 | 98 |
| 7 |  | 70 | 5 | >99 |
| 8 | 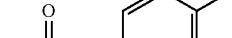 | 70 | 5 | >99 |
| 9 | 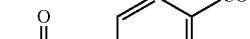 | 70 | 5 | 81(>99[c]) |
| 10 | 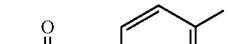 | 70 | 5 | 97 |
| 11 | 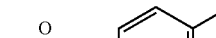 | 70 | 5 | >99 |

TABLE 6-1-continued

| Entry No. | Amide | Reaction Temperature (° C.) | Reaction Time (hr.) | Yield (%)[a] |
|---|---|---|---|---|
| 12 | 4-Br-C6H4-NHC(O)CH3 | 70 | 5 | 96 |
| 13 | 4-OMOM-C6H4-NHC(O)CH3 | 70 | 5 | 99 |
| 14 | 4-(CH2OMEM)-C6H4-NHC(O)CH3 | 70 | 5 | 89 |

[a] Isolation Yield
[b] Ammonium bromide was 10 mol %.
[c] The yield was determined by $^1$H NMR analysis of the reaction mixture.

TABLE 6-2

| Entry No. | Amide | Reaction Temperature (° C.) | Reaction Time (hr.) | Yield (%)[a] |
|---|---|---|---|---|
| 15 | 4-(CH2OTHP)-C6H4-NHC(O)CH3 | 70 | 5 | 93 |
| 16 | 4-(CH2OTIPS)-C6H4-NHC(O)CH3 | 70 | 5 | 83 |
| 17 | N-acetyl-1,2,3,4-tetrahydroisoquinoline | 70 | 5 | >99 |
| 18 | N-benzyl-N-methylacetamide | 80 | 10 | 95 |
| 19 | N-benzyl-N-ethylacetamide | 100 | 15 | 85[b] |
| 20 | N-(1-adamantyl)acetamide | 100 | 5 | 93 |

TABLE 6-2-continued

| Entry No. | Amide | Reaction Temperature (° C.) | Reaction Time (hr.) | Yield (%)[a] |
|---|---|---|---|---|
| 21 | N,N-dibenzylformamide | 80 | 10 | 97 |
| 22 | N-(4-phenylbutyl)benzamide | 100 | 5 | 87 |
| 23 | 2-benzoyl-1,2,3,4-tetrahydroisoquinoline | 90 | 5 | 94 |
| 24 | 2-(pyridine-2-carbonyl)-1,2,3,4-tetrahydroisoquinoline | 60 | 5 | 91 |
| 25 | N-benzylpropanamide | 80 | 5 | 89[b] |
| 26 | N-benzyl-2,2,2-trichloroacetamide | 60 / 80 | 3 / +3 | >99[b] |
| 27 | N-benzyl-2-chloroacetamide | 50 | 5 | 87 |
| 28 | (2,3-dihydro-1H-indol-1-yl)(pyridin-2-yl)methanone | 50 | 5 | 96 |

[a]Isolation Yield
[b]Ammonium bromide was 10 mol %.

[C.F. 10]

Entry 1

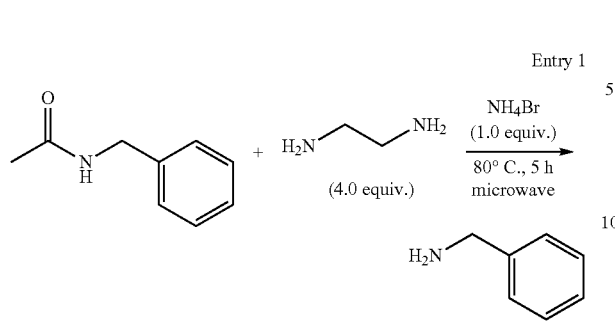

Dichloromethane and 1 M hydrochloric acid aqueous solution were added to the reaction mixture for separation with separatory funnel. The aqueous layer was basified with sodium hydroxide aqueous solution, followed by the extraction of the target amine with ether. The organic layer was dried over sodium sulfate, and then the solvent was removed by rotary evaporation to obtain a yellow liquid product. Yield 96.6 mg (90%).

$^1$H NMR (400 MHz, CDCl$_3$) δ 7.38-7.22 (m, 5H), 3.87 (s, 2H), 1.56 (br, 2H); $^{13}$C NMR (100 MHz, CDCl$_3$) δ 143.14, 128.51, 127.02, 126.77, 46.41.

[C.F. 11]

Entry 2

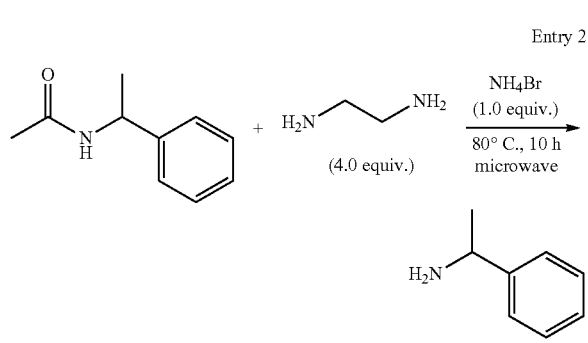

Dichloromethane and 1 M hydrochloric acid aqueous solution were added to the reaction mixture for separation with separatory funnel. The aqueous layer was basified with sodium hydroxide aqueous solution, followed by the extraction of the target amine with ether. The organic layer was dried over sodium sulfate, and then the solvent was removed by rotary evaporation to obtain a yellow liquid product. Yield 106 mg (87%).

$^1$H NMR (400 MHz, CDCl$_3$) δ 7.42-7.22 (m, 5H), 4.12 (q, J=6.4 Hz, 2H), 1.39 (d, J=6.4 Hz, 2H), 1.56 (br, 2H); $^{13}$C NMR (100 MHz, CDCl$_3$) δ 147.96, 128.70, 127.02, 125.88, 51.55, 25.87.

[C.F. 12]

Entry 3

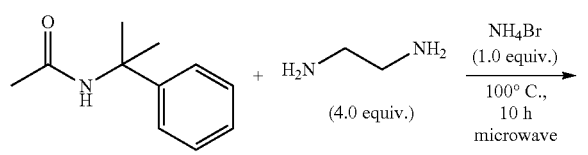

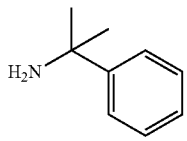

Dichloromethane and 1 M hydrochloric acid aqueous solution were added to the reaction mixture for separation with separatory funnel. The aqueous layer was basified with sodium hydroxide aqueous solution, followed by the extraction of the target amine with ether. The organic layer was dried over sodium sulfate, and then the solvent was removed by rotary evaporation to obtain a yellow liquid product. Yield 119 mg (88%).

$^1$H NMR (400 MHz, CDCl$_3$) δ 7.54-7.48 (m, 2H), 7.34 (t, J=7.6 Hz, 2H), 7.22 (t, J=7.6 Hz, 1H), 1.60 (br, 2H), 1.50 (s, 6H); $^{13}$C NMR (100 MHz, CDCl$_3$) δ 150.18, 128.16, 126.14, 124.57, 52.35, 32.69.

[C.F. 13]

Entry 4

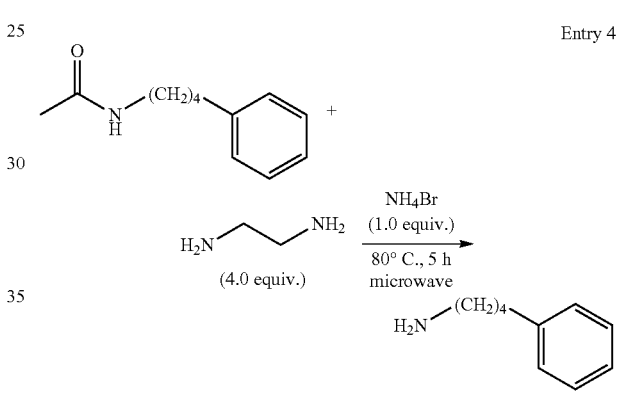

Dichloromethane and 1 M hydrochloric acid aqueous solution were added to the reaction mixture for separation with separatory funnel. The aqueous layer was basified with sodium hydroxide aqueous solution, followed by the extraction of the target amine with ether. The organic layer was dried over sodium sulfate, and then the solvent was removed by rotary evaporation to obtain a yellow liquid product. Yield 132 mg (89%).

$^1$H NMR (400 MHz, CDCl$_3$) δ 7.27-7.15 (m, 5H), 2.71 (t, J=7.2 Hz, 2H), 2.63 (t, J=7.2 Hz, 2H), 1.71-1.40 (m, 6H); $^{13}$C NMR (100 MHz, CDCl$_3$) δ 142.24, 128.33, 128.16, 125.71, 41.34, 35.62, 32.01, 28.59.

[C.F. 14]

Entry 5

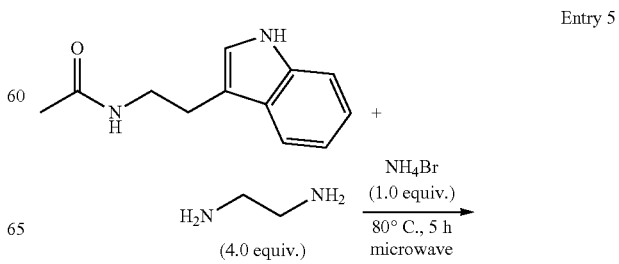

-continued

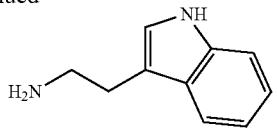

The reaction mixture was directly purified by silica gel column chromatography (dichloromethane:hexane:diethylamine=100:10:5), followed by removal of the solvents by rotary evaporation. Then 1 M NaOH aqueous solution and ethyl acetate were added for separation with separatory funnel. The organic layer was dried over sodium sulfate, followed by removal of the solvents by rotary evaporation to obtain pale red solid product. Yield 130 mg (81%).

$^1$H NMR (400 MHz, DMSO-$d_6$) δ 10.8 (br, 1H), 7.65 (brd, J=7.6 Hz, 1H), 7.32 (brd, J=8.0 Hz, 1H), 6.62-6.50 (d, J=2.4 Hz, 1H), 7.05 (dd, J=1.2, 8.0 Hz, 1H), 6.95 (dd, J=1.2, 7.6 Hz, 1H), 2.82-2.71 (m, 4H), 2.52 (br, 2H); $^{13}$C NMR (100 MHz, CDCl$_3$) δ 136.31, 127.38, 122.63, 120.86, 118.38, 118.26, 112.60, 111.37, 42.73, 29.48.

[C.F. 15]

Entry 6

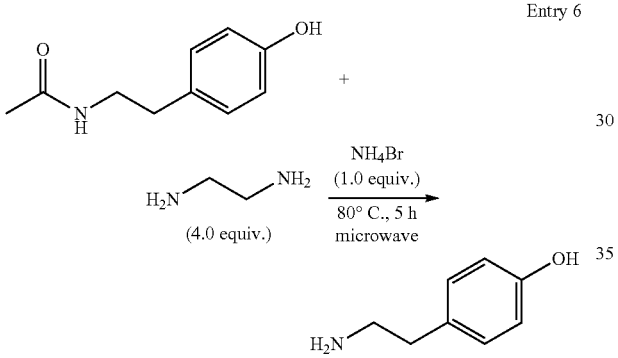

The reaction mixture was directly purified by silica gel column chromatography (dichloromethane:hexane:diethylamine=100:10:5), followed by drying at 80° C. under vacuum to obtain pale red solid product. Yield 135 mg (98%).

$^1$H NMR (400 MHz, DMSO-$d_6$) δ 7.02 (d, J=8.4 Hz, 2H), 6.70 (d, J=8.4 Hz, 2H), 3.34 (br, 3H), 2.89 (t, J=7.6 Hz, 2H), 2.67 (br, 3H), 2.67 (t, J=7.6 Hz, 2H); $^{13}$C NMR (100 MHz, CDCl$_3$) δ 155.95, 129.52, 128.01, 115.27, 41.23, 33.97.

Entry 7

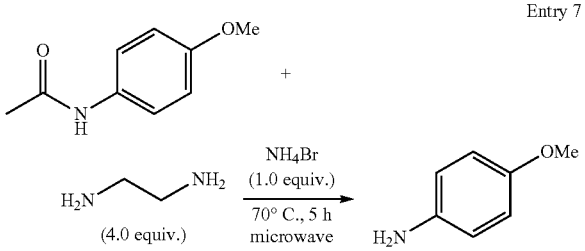

The reaction mixture was directly purified by silica gel column chromatography (dichloromethane) to obtain a pale red solid product. Yield 123 mg (100%).

$^1$H NMR (400 MHz, CDCl$_3$) δ 6.75 (d, J=8.8 Hz, 2H), 6.65 (d, J=8.8 Hz, 2H), 3.74 (s, 2H), 3.34 (br, 2H); $^{13}$C NMR (100 MHz, CDCl$_3$) δ 152.78, 139.93, 116.36, 114.80, 55.70.

[C.F. 17]

Entry 8

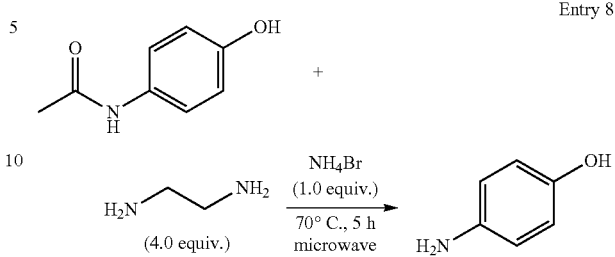

The reaction mixture was directly purified by silica gel column chromatography (ether) to obtain a white solid product. Yield 109 mg (100%).

$^1$H NMR (400 MHz, DMSO-$d_6$) δ 8.23 (s, 1H), 6.50-6.78 (m, 4H), 4.34 (s, 2H); $^{13}$C NMR (100 MHz, DMSO-$d_6$) δ 148.21, 140.62, 115.53, 115.22.

[C.F. 18]

Entry 9

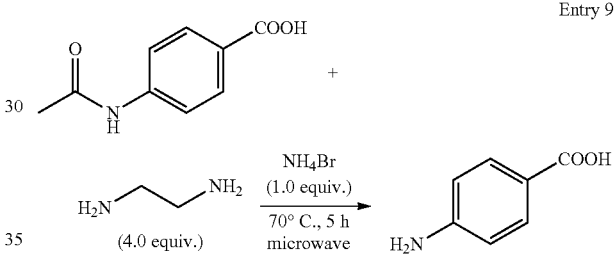

The reaction mixture was directly purified by silica gel column chromatography (ethyl acetate:methanol=10:1) to obtain a white solid product. Yield 111 mg (81%).

$^1$H NMR (400 MHz, DMSO-$d_6$) δ 7.60 (d, J=8.8 Hz, 2H), 6.53 (d, J=8.8 Hz, 2H), 5.84 (s, 1H); $^{13}$C NMR (100 MHz, DMSO-$d_6$) δ 167.48, 153.12, 131.12, 116.91, 112.56.

[C.F. 19]

Entry 10

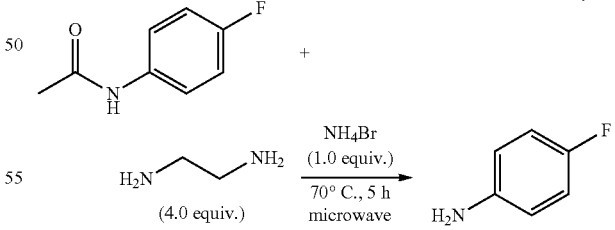

The reaction mixture was subjected to separation with separatory funnel with water and ether. The organic layer was dried over sodium sulfate, and then the solvent was removed by rotary evaporation to obtain a yellow liquid product. Yield 108 mg (98%).

$^1$H NMR (400 MHz, CDCl$_3$) δ 6.89-6.81 (m, 2H), 6.65-6.57 (m, 2H), 3.52 (br, 2H); $^{13}$C NMR (100 MHz, CDCl$_3$) δ 157.78, 155.41, 142.52, 116.04.

[C.F. 20]

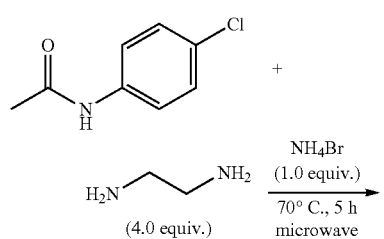

Entry 11

The reaction mixture was directly purified by silica gel column chromatography (ether:hexane=1:1) to obtain a white solid product. Yield 127 mg (100%).

¹H NMR (400 MHz, CDCl₃) δ 7.12-7.08 (m, 2H), 6.63-6.57 (m, 2H), 3.64 (br, 2H); ¹³C NMR (100 MHz, CDCl₃) δ 145.07, 129.24, 123.29, 116.34.

[C.F. 21]

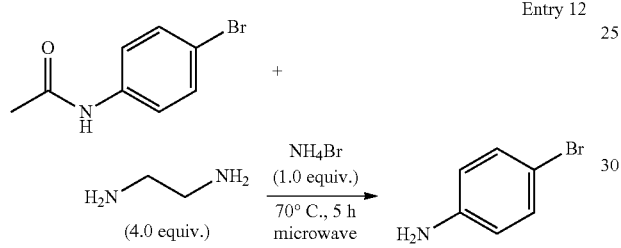

Entry 12

The reaction mixture was subjected to separation with separatory funnel with sodium hydrogen carbonate aqueous solution and ether. The organic layer was dried over sodium sulfate, and then the solvent was removed by rotary evaporation. The resultant crude mixture was then purified by silica gel column chromatography (ether:hexane=1:1) to obtain a white solid product. Yield 166 mg (96%).

¹H NMR (400 MHz, CDCl₃) δ 7.30-7.12 (m, 2H), 6.62-6.50 (m, 2H), 3.66 (br, 2H); ¹³C NMR (100 MHz, CDCl₃) δ 145.41, 132.00, 116.67, 110.18.

[C.F. 22]

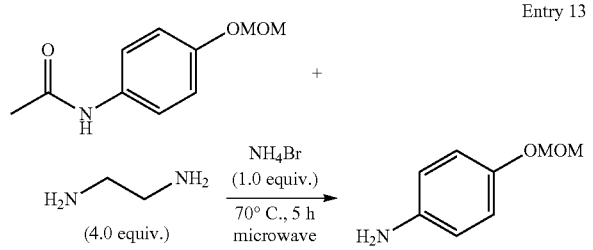

Entry 13

The reaction mixture was subjected to separation with separatory funnel with water and ether. The organic layer was dried over sodium sulfate, and then the solvent was removed by rotary evaporation to obtain a yellow liquid product. Yield 151 mg (99%).

¹H NMR (400 MHz, CDCl₃) δ 6.90-6.84 (m, 2H), 6.66-6.60 (m, 2H), 5.08 (s, 2H), 3.48 (s, 3H), 3.47 (br, 2H); ¹³C NMR (100 MHz, CDCl₃) δ 150.15, 141.18, 117.89, 116.15, 95.46, 55.74.

[C.F. 23]

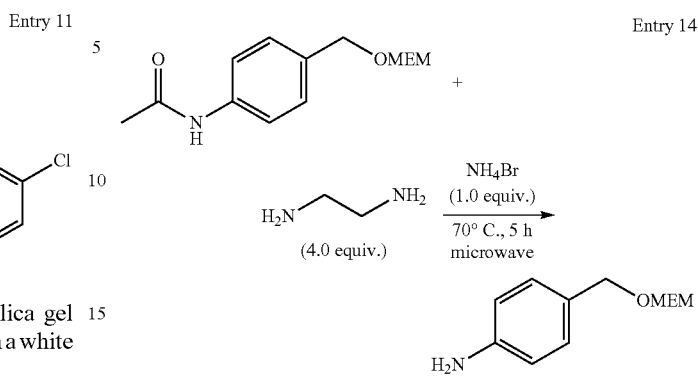

Entry 14

The reaction mixture was directly purified by silica gel column chromatography (ether) to obtain a colorless, transparent liquid product. Yield 188 mg (89%).

¹H NMR (400 MHz, CDCl₃) δ 7.14 (d, J=8.4 Hz, 2H), 6.66 (d, J=8.4 Hz, 2H), 4.77 (s, 2H), 4.50 (s, 2H), 3.73 (m, 2H), 3.68 (br, 2H), 3.58 (m, 2H), 3.41 (s, 3H); ¹³C NMR (100 MHz, CDCl₃) δ 146.10, 129.58, 127.47, 114.83, 94.29, 71.70, 69.16, 66.69, 58.86.

[C.F. 24]

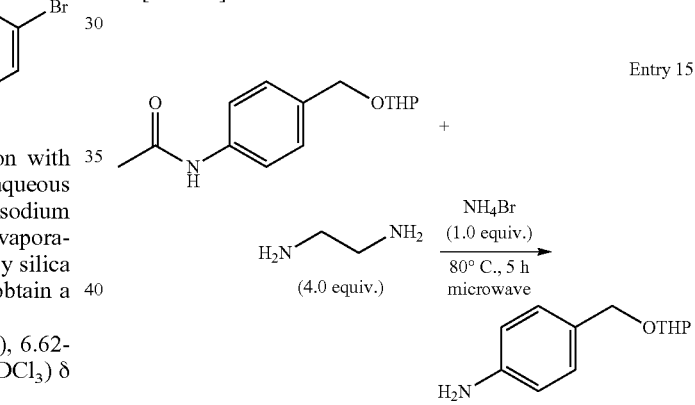

Entry 15

The reaction mixture was directly purified by silica gel column chromatography (dichloromethane:hexane:diethylamine=100:5:5), and then the solvent was removed by distillation to obtain a pale yellow liquid product. Yield 192 mg (93%).

¹H NMR (400 MHz, CDCl₃) δ 7.15 (d, J=8.4 Hz, 2H), 6.64 (d, J=8.4 Hz, 2H), 4.70-4.65 (m, 1H), 4.66 (d, J=11.2 Hz, 2H), 4.38 (d, J=11.2 Hz, 2H), 3.96 (m, 1H), 3.65 (br, 2H), 3.56-3.48 (m, 1H), 1.90-1.43 (m, 6H); ¹³C NMR (100 MHz, CDCl₃) δ 146.26, 129.86, 128.29, 115.18, 97.52, 69.01, 62.36, 30.90, 25.78, 19.73.

[C.F. 25]

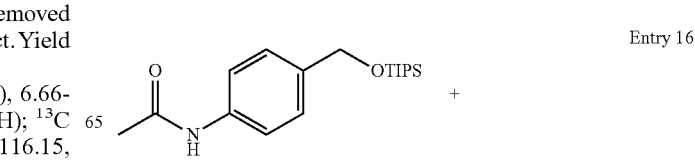

Entry 16

The reaction mixture was subjected to separation with separatory funnel with water and ether. The organic solvent was dried over sodium sulfate, followed by removal of the solvent by rotary evaporation. The resultant crude mixture was then purified by silica gel column chromatography (from ethyl acetate: hexane=1:5 to 3:5), and the solvent was removed by rotary evaporation to obtain pale a yellow liquid product. Yield 185 mg (83%). The starting material was recovered in 10% (the reaction on 0.80 mmol scale).

$^1$H NMR (400 MHz, CDCl$_3$) δ 7.14 (d, J=8.8 Hz, 2H), 6.66 (d, J=8.8 Hz, 2H), 4.71 (s, 2H) 3.61 (br, 2H), 1.14 (m, 2H), 1.08 (d, J=6.0 Hz, 18H); $^{13}$C NMR (100 MHz, CDCl$_3$) δ 145.17, 131.86, 127.24, 114.95, 64.97, 18.01, 12.09.

[C.F. 26]

Entry 17

The reaction mixture was subjected to separation with separatory funnel with dichloromethane and 1 M hydrochloric acid aqueous solution, and then the water layer was basified with sodium hydroxide aqueous solution, followed by extraction with ether. The organic layer was dried over sodium sulfate, and then the solvent was removed by distillation to obtain a yellow liquid product. Yield 133 mg (100%).

$^1$H NMR (400 MHz, CDCl$_3$) δ 7.16-6.94 (m, 4H), 4.02 (s, 2H), 3.14 (t, J=6.0 Hz, 2H), 2.80 (t, J=6.0 Hz, 2H), 1.66 (br, 1H); $^{13}$C NMR (100 MHz, CDCl$_3$) δ 135.83, 134.68, 129.27, 126.16, 125.98, 125.68, 48.21, 43.81, 29.09.

[C.F. 27]

Entry 18

The reaction mixture was subjected to funnel separation with 1 M sodium hydroxide and ether. The organic layer was dried over sodium hydroxide, and then the solvent was removed by distillation to obtain a yellow liquid product. Yield 115 mg (95%).

$^1$H NMR (400 MHz, CDCl$_3$) δ 7.36-7.22 (m, 5H), 3.75 (s, 2H), 2.46 (s, 3H), 1.56 (br, 2H); $^{13}$C NMR (100 MHz, CDCl$_3$) δ 140.05, 128.36, 128.15, 126.95, 56.04, 35.93.

Entry 19

After termination of the reaction, the reaction mixture was analyzed directly by $^1$H NMR spectroscopy in which the yield was calculated on the integrated intensity ratio of the starting materials and the product in $^1$H NMR spectrum. Yield 85%.

[C.F. 28]

Entry 20

The reaction mixture was subjected to separation with separatory funnel with dichloromethane and 1 M hydrochloric acid aqueous solution, and then the aqueous layer was basified with sodium hydroxide aqueous solution, followed by extraction with ether. The organic layer was dried over sodium sulfate, and then the solvent was removed by rotary evaporation to obtain a white solid product. Yield 140 mg (93%).

$^1$H NMR (400 MHz, CDCl$_3$) δ 2.05 (br, 3H), 1.69-1.54 (m, 12H) 1.13 (br, 2H); $^{13}$C NMR (100 MHz, CDCl$_3$) δ 47.19, 46.31, 36.28, 29.90.

[C.F. 29]

Entry 21

The reaction mixture was directly purified by silica gel column chromatography (from hexane:ethyl acetate:diethylamine=10:3:0.1 to 1:1:0.1) to obtain a colorless, transparent liquid product. Yield 192 mg (97%). $^1$H NMR (400 MHz, (CD$_3$)$_2$SO) δ 7.48-7.45 (m, 10H), 3.82 (s, 4H) 1.56 (br, 1H); $^{13}$C NMR (100 MHz, (CD$_3$)$_2$SO) δ 140.87, 128.87, 128.62, 127.41, 53.67.

[C.F. 30]

Entry 22

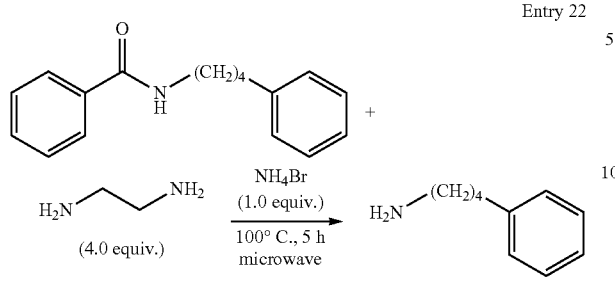

The reaction mixture was subjected to separation with separatory funnel with dichloromethane and 1 M sodium hydroxide, and then the aqueous layer was basified with sodium hydroxide aqueous solution, followed by extraction of the target amine with ether. The organic layer was dried over sodium sulfate, and then the solvent was removed by rotary evaporation to obtain a yellow liquid product. Yield 130 mg (87%).

$^1$H NMR (400 MHz, CDCl$_3$) δ 7.29-7.27 (m, 3H), 7.19-7.15 (m, 2H), 2.71 (t, J=7.2 Hz, 2H), 2.63 (t, J=7.2 Hz, 2H), 1.66 (tt, J=7.2, 7.2 Hz, 2H), 1.48 (tt, J=7.2, 7.2 Hz, 2H); $^{13}$C NMR (100 MHz, CDCl$_3$) δ 142.48, 128.36, 128.35, 125.66, 42.13, 35.76, 33.49, 28.72.

[C.F. 31]

Entry 23

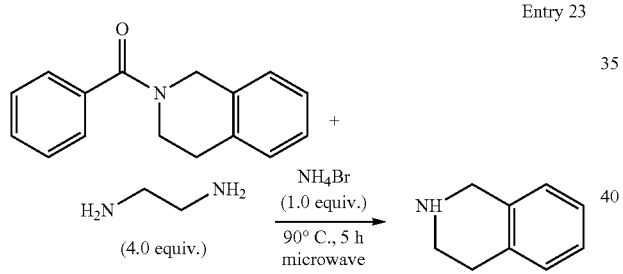

The reaction mixture wad directly purified by silica gel column chromatography (dichloromethane:methanol:diethylamine=10:0.5:0.1). The solvent was removed by rotary evaporation, and then the impurities are precipitated with hexane for filtration. The solvent of the filtrate was removed by rotary evaporation to obtain a yellow liquid product. Yield 125 mg (94%).

$^1$H NMR (400 MHz, CDCl$_3$) δ 7.14-6.95 (m, 3H), 7.02-6.96 (m, 1H), 4.02 (s, 2H), 3.14 (t, J=6.0 Hz, 2H), 2.80 (t, J=6.0 Hz, 2H), 1.60 (br, 1H); $^{13}$C NMR (100 MHz, CDCl$_3$) δ 135.83, 134.68, 129.27, 126.16, 125.98, 125.68, 48.21, 43.81, 29.09.

[C.F. 32]

Entry 24

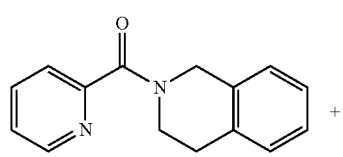

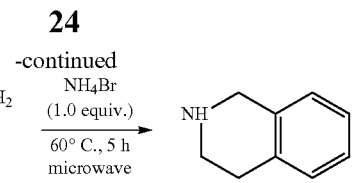

The reaction mixture was subjected to separation with separatory funnel with water and ether. The organic layer was dried over sodium sulfate, and then the solvent was removed by rotary evaporation. The impurities are then precipitated with hexane for filtration, and the solvent of the filtrate was removed by rotary evaporation to obtain a yellow liquid product. Yield 121 mg (91%).

$^1$H NMR (400 MHz, CDCl$_3$) δ 7.15-7.05 (m, 3H), 7.03-6.98 (m, 1H), 4.02 (s, 2H), 3.14 (t, J=6.0 Hz, 2H), 2.80 (t, J=6.0 Hz, 2H), 1.60 (br, 1H); $^{13}$C NMR (100 MHz, CDCl$_3$) δ 135.86, 134.71, 129.25, 126.15, 125.96, 125.67, 48.22, 43.81, 29.11.

Entry 25

After termination of the reaction, the reaction mixture was directly analyzed by $^1$H NMR spectroscopy in which the yield was calculated on the integrated intensity ratio of the starting materials and the product in $^1$H NMR spectrum. Yield 89%.

Entry 26

After termination of the reaction, the reaction mixture was directly analyzed by $^1$H NMR spectroscopy in which the yield was calculated on the integrated ratio of the starting materials and the product in $^1$H NMR spectrum. Yield more than 99%.

[C.F. 33]

Entry 27

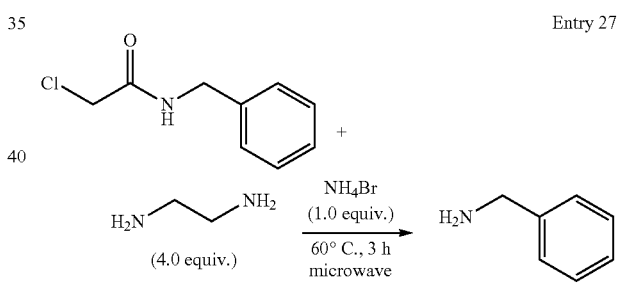

The reaction mixture was subjected to separation with separatory funnel with dichloromethane and 1 M hydrochloric acid aqueous solution. The water layer was basified with sodium hydroxide aqueous solution, and the target amine was extracted with ether. The organic layer was dried over sodium sulfate, and then the solvent was removed by rotary evaporation to obtain a yellow liquid product. Yield 93.1 mg (90%).

$^1$H NMR (400 MHz, CDCl$_3$) δ 7.38-7.22 (m, 5H), 3.86 (s, 2H), 1.61 (br, 2H); $^{13}$C NMR (100 MHz, CDCl$_3$) δ 143.24, 128.51, 127.04, 118.37, 46.46.

[C.F. 34]

Entry 28

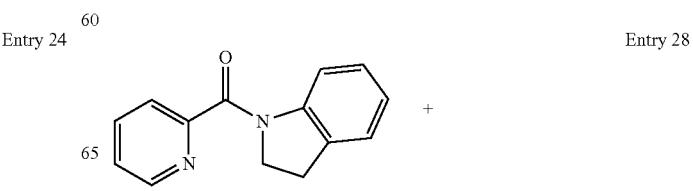

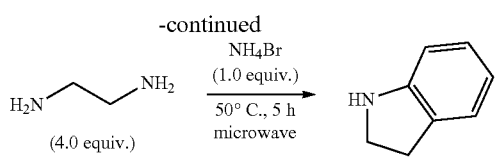

¹H NMR (400 MHz, CDCl₃) δ 7.11 (d, J=7.2 Hz, 1H), 7.01 (m, 1H), 6.70 (dd, J=7.2, 0.8 Hz, 1H), 6.64 (d, J=7.6 Hz, 1H), 3.70 (br, 1H), 3.55 (t, J=8.4 Hz, 2H), 3.03 (t, J=8.4 Hz, 2H); ¹³C NMR (100 MHz, CDCl₃) δ 151.54, 129.21, 127.00, 124.70, 118.38, 109.32, 47.23, 29.77.

Example 3

Deacylation Using Ethylene Diamine (No. 2)

As shown by the reaction equation below, deacylation reaction was applied to the synthesis of chiral amines.
[C.F. 35]

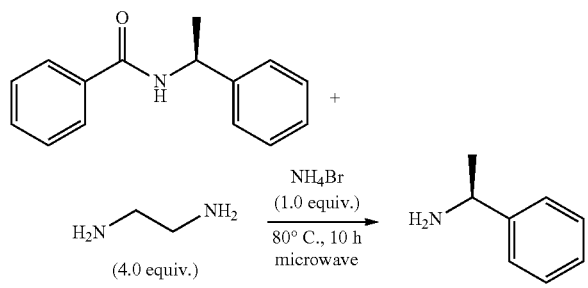

Dichloromethane and 1 M hydrochloric acid aqueous solution were added to the reaction mixture for separation with separatory funnel. The aqueous layer was basified with sodium hydroxide aqueous solution, followed by the extraction of the target amine with ether. The organic layer was dried over sodium sulfate, and then the solvent was removed by rotary evaporation to obtain a yellow liquid product. Yield 113 mg (93%).

¹H NMR (400 MHz, CDCl₃) δ 7.36-7.31 (m, 4H), 7.25-7.22 (m, 1H), 4.11 (q, J=7.8 Hz, 1H), 1.55 (br, 2H), 1.39 (d, J=7.8 Hz, 3H); ¹³C NMR (100 MHz, CDCl₃) δ 147.83, 128.45, 126.75, 125.65, 51.32, 25.68.
[C.F. 36]

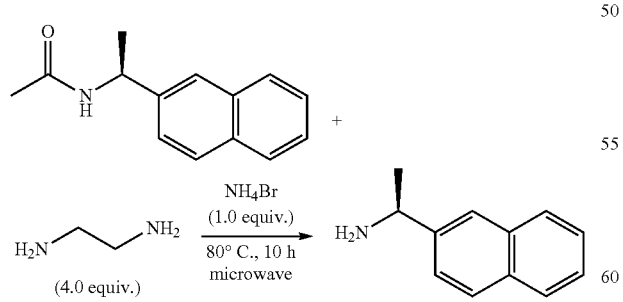

Dichloromethane and 1 M hydrochloric acid aqueous solution were added to the reaction mixture for separation with separatory funnel. The aqueous layer was basified with sodium hydroxide aqueous solution, followed by the extraction of the target amine with ether. The organic layer was dried over sodium sulfate, and then the solvent was removed by rotary evaporation to obtain a yellow liquid product. Yield 154 mg (90%).

¹H NMR (400 MHz, CDCl₃) δ 8.13 (d, J=8.4 Hz, 1H), 7.87 (d, J=7.6 Hz, 1H), 7.75 (d, J=8.4 Hz, 1H), 7.70 (d, J=7.6 Hz, 1H), 7.53-7.25 (m, 3H), 4.95 (q, J=6.4 Hz, 1H), 1.60 (br, 2H), 1.56 (d, J=6.4 Hz, 3H); ¹³C NMR (100 MHz, CDCl₃) δ 142.26, 133.88, 130.72, 128.93, 127.19, 125.90, 125.59, 125.38, 122.89, 121.35, 46.46, 24.82.

Example 4

Deacylation Using Hydrazine

As shown by the reaction equations below, deacylation reactions were carried out with respect to various amides using hydrazine. No microwave irradiation was applied in all the reactions shown below.
[C.F. 37]

Entry 1

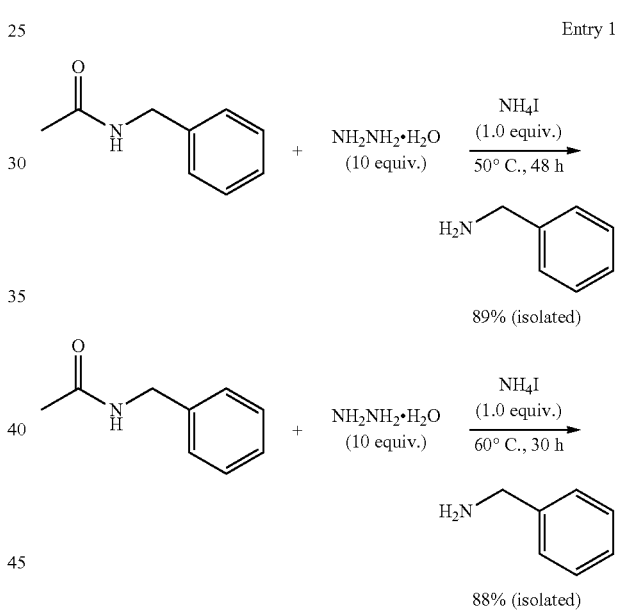

The reactions were conducted at 50° C. for 48 hours, and at 60° C. for 30 hours, respectively. Separation with separatory funnel was carried out with HCl aqueous solution and dichloromethane, and then the aqueous layer was basified with NaOH aqueous solution, followed by the extraction with diethyl ether to obtain a yellow liquid product. Yield 95 mg (89%) and Yield 94 mg (88%).
[C.F. 38]

Entry 2

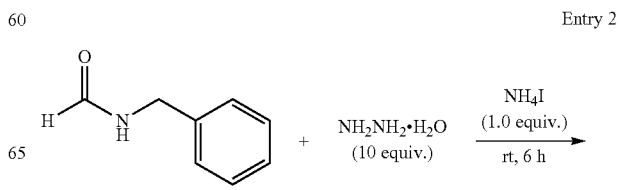

-continued

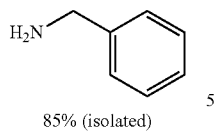

85% (isolated)

Following separation with separatory funnel with NaOH aqueous solution and ether, 7 mL of 1 M HCl in diethyl ether was added for stirring overnight at room temperature. Filtration was then conducted to obtain a white solid product. Yield 122 mg (85% as hydrochloride salt).

[C.F. 39]

Entry 3

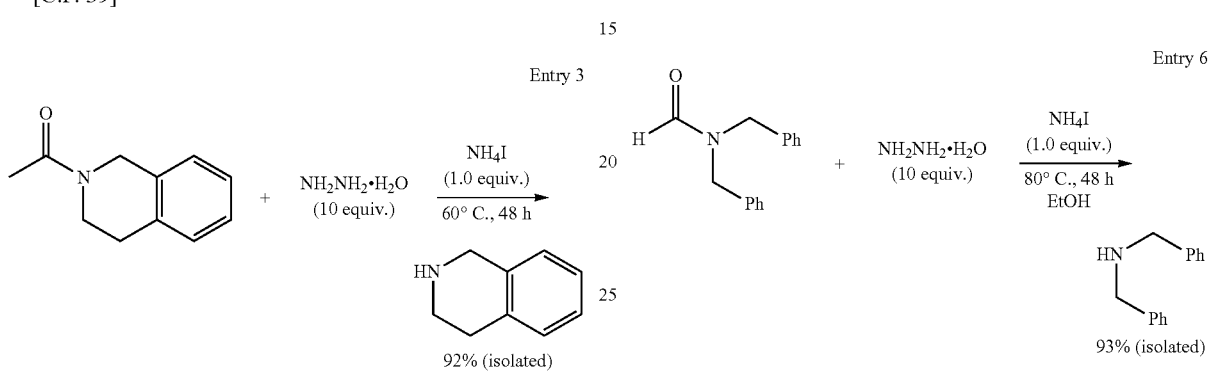

92% (isolated)

Separation with separatory funnel was conducted with ether and NaOH aqueous solution to obtain a pale yellow liquid product. Yield 123 mg (87%).

[C.F. 40]

Entry 4

87% (isolated)

Separation with separatory funnel was carried out with HCl aqueous solution and dichloromethane, and then the water layer was basified with NaOH aqueous solution, followed by separation with separatory funnel with diethyl ether to obtain a pale yellow liquid product. Yield 106 mg (87%).

[C.F. 41]

Entry 5

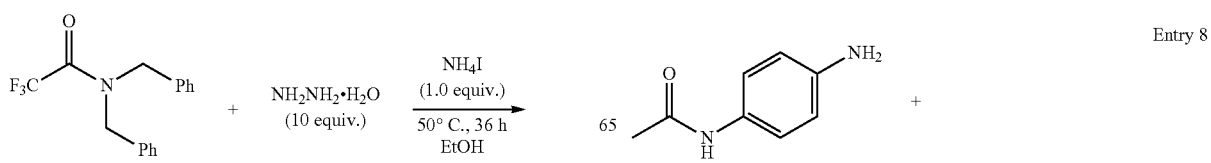

-continued

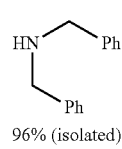

96% (isolated)

The reaction mixture was purified by column chromatography with ethyl acetate/hexane (1/1) to obtain a pale yellow liquid product. Yield 189 mg (96%).

[C.F. 42]

Entry 6

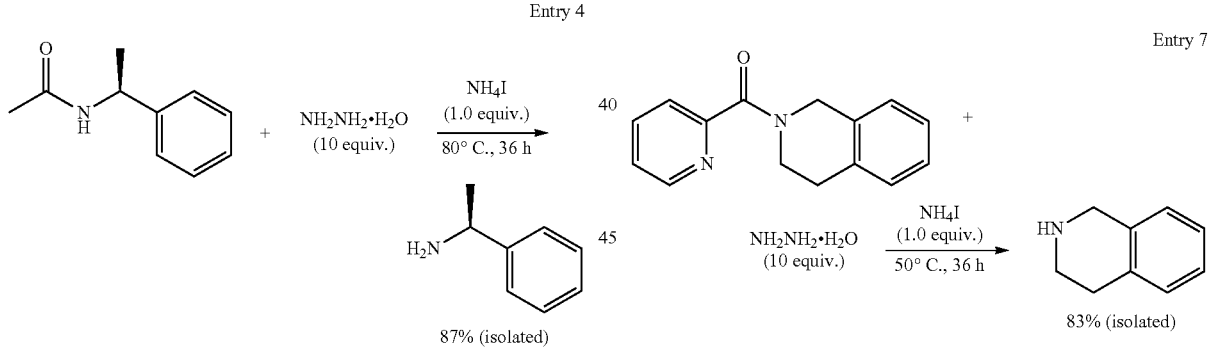

93% (isolated)

After separation with separatory funnel with NaHCO₃ aqueous solution and ether, purification by column chromatography was carried out to obtain a yellow liquid product. Yield 184 mg (93%).

[C.F. 43]

Entry 7

83% (isolated)

After separation with separatory funnel with HCl aqueous solution and dichloromethane, the aqueous layer was basified with NaOH aqueous solution, followed by back-extraction with diethyl ether. The ether was removed by rotary evaporation and hexane was added for filtration. The hexane in the filtrate was removed to obtain a yellow liquid product. Yield 112 mg (83%).

[C.F. 44]

Entry 8

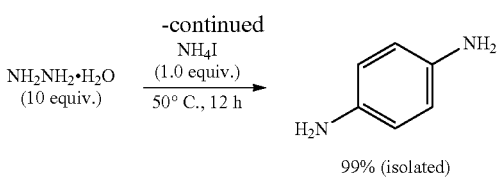

99% (isolated)

Purification by column chromatography (from ethyl acetate/hexane=2/1 to ethyl acetate only) provided a pale read solid product. Yield 107 mg (99%).

[C.F. 45]

Entry 9

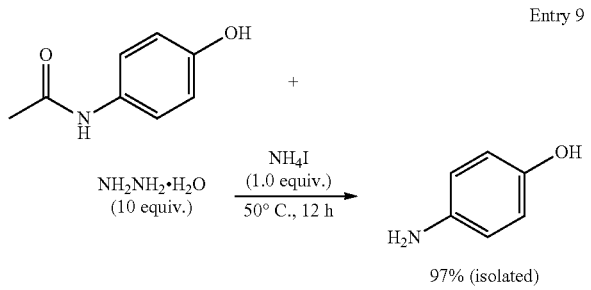

97% (isolated)

Purification by column chromatography (from ethyl acetate/hexane=1/2 to 1/1) provided a white solid product. Yield 106 mg (97%).

[C.F. 46]

Entry 10

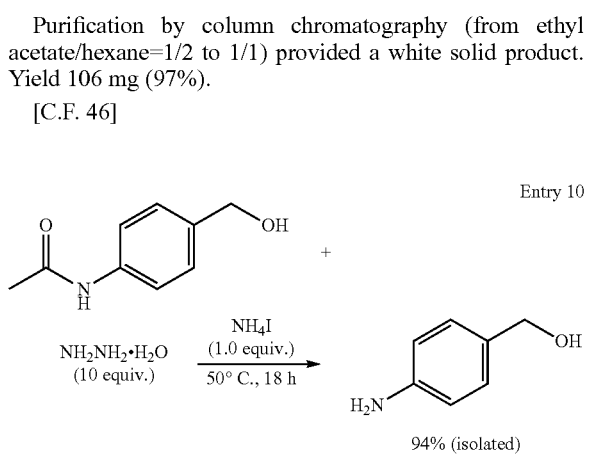

94% (isolated)

Purification by column chromatography (ethyl acetate/hexane=2/1) provided a white solid product. Yield 116 mg (94%).

[C.F. 47]

Entry 11

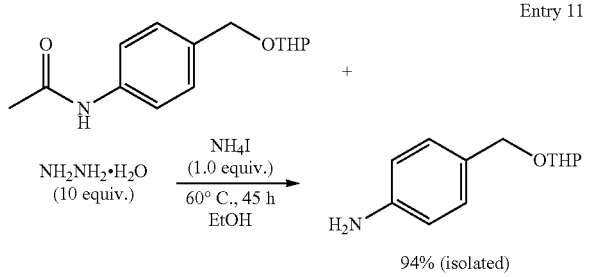

94% (isolated)

Purification by column chromatography (ethyl acetate/hexane=½) provided a pale yellow liquid product. Yield 195 mg (94%).

[C.F. 48]

Entry 12

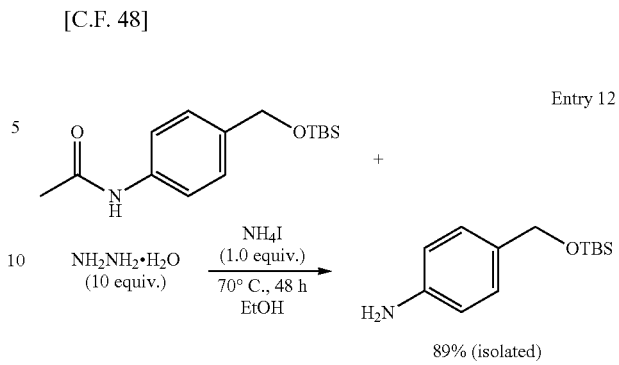

89% (isolated)

Purification by column chromatography (ethyl acetate/hexane=7/23) provided a colorless, transparent liquid product. Yield 211 mg (89%).

$^1$H NMR (400 MHz, CDCl$_3$) δ 7.11 (d, J=8.4 Hz, 2H), 6.65 (d, J=8.4 Hz, 2H), 4.62 (s, 2H), 3.56 (br, 2H), 0.92 (s, 9H), 0.07 (s, 6H).

[C.F. 49]

Entry 13

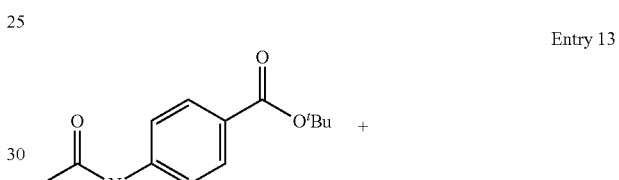

85% (isolated)

Purification by column chromatography (ethyl acetate/hexane=½) provided a white solid product. Yield 165 mg (85%).

$^1$H NMR (400 MHz, CDCl$_3$) δ 7.77-7.83 (m, 2H), 6.59-6.65 (m, 2H), 3.82 (br, 2H), 1.57 (s, 9H).

[C.F. 50]

Entry 14

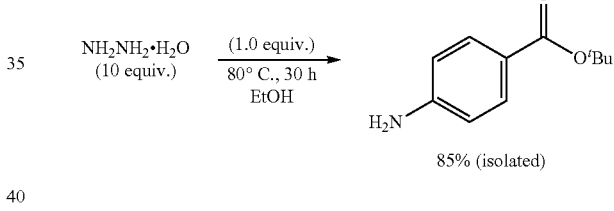

94% (isolated)

Purification by column chromatography (from ethyl acetate/hexane=2/1 to 1/1) provided a yellow solid product. Yield 130 mg (94%).

$^1$H NMR (400 MHz, CDCl$_3$) δ 8.07 (d, J=8.4 Hz, 2H), 6.62 (d, J=8.4 Hz, 2H), 4.33 (br, 2H).

[C.F. 51]

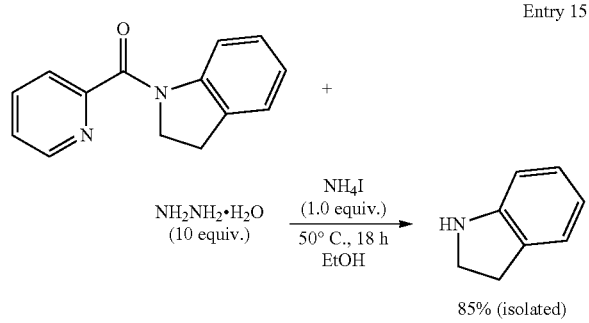

Entry 15

85% (isolated)

The reaction mixture was purified by column chromatography with ethyl acetate/hexane (¼) to obtain a colorless liquid product. Yield 101 mg (85%). 2 mg of the starting material was recovered.

[C.F. 52]

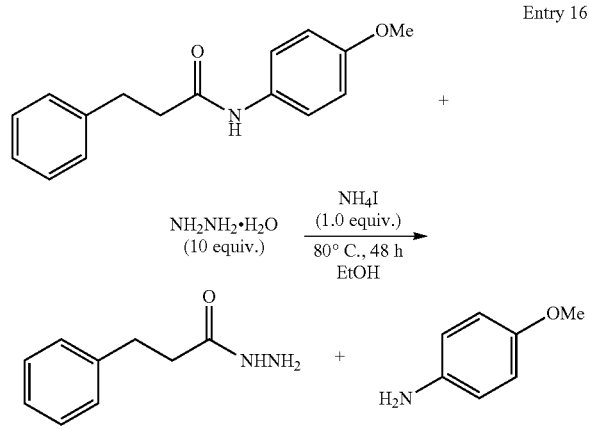

Entry 16

The reaction mixture was purified by column chromatography with ethyl acetate/hexane (½), ethyl acetate only, and then ethyl acetate/methyl alcohol (10/1) to obtain a while solid product. Yield (the aniline) 96 mg (78%). Yield (the hydrazide) 134 mg (82%).

Hydrazide $^1$H NMR (400 MHz, CDCl$_3$) δ 7.45-7.15 (m, 5H), 6.53 (br, 1H), 3.85 (br, 2H), 2.98 (t, J=7.6 Hz, 2H), 2.45 (t, J=7.6 Hz, 2H).

[C.F. 53]

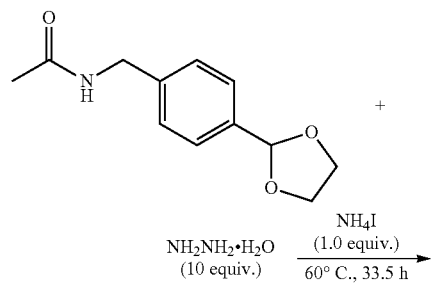

Entry 18

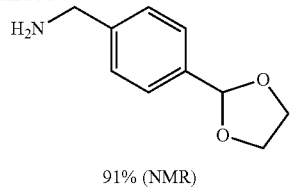

91% (NMR)

A side reaction occurred in the case of using ethylenediamine as the reactant, whereas by using hydrazine there was observed no side reaction as in the use of ethylenediamine and the reaction proceeded smoothly. Yield by $^1$H NMR analysis was 91%.

Example 5

Decarbonylation Using Alkylamines (No. 1)

As shown by the reaction equations below, decarbonylation reactions (including dethiocarbonylation reactions) were carried out using alkylamines. The results are summarized in Table 7.

TABLE 7

| Entry | Carbamate | Temp. [° C.] | Time [h] | Yield [%][a] |
|---|---|---|---|---|
| 1 | 3y039 | 90 | 5 | 92 |
| 2 | 3y041 | 90 | 5 | 84 |
| 3 | 3y040 | 90 | 5 | 85 |
| 4[b] | | 80 | 5 | 99 |
| 5[b] | NSM137 | 70 | 2 | 95 |

TABLE 7-continued

| Entry | Carbamate | Temp. [° C.] | Time [h] | Yield [%]$^a$ |
|---|---|---|---|---|
| 6$^b$ | 3y005 | 80 | 5 | 91 |

$^a$Isolation yield
$^b$Ethylene diamine was used.

[C.F. 54]

(3y039)

Entry 1

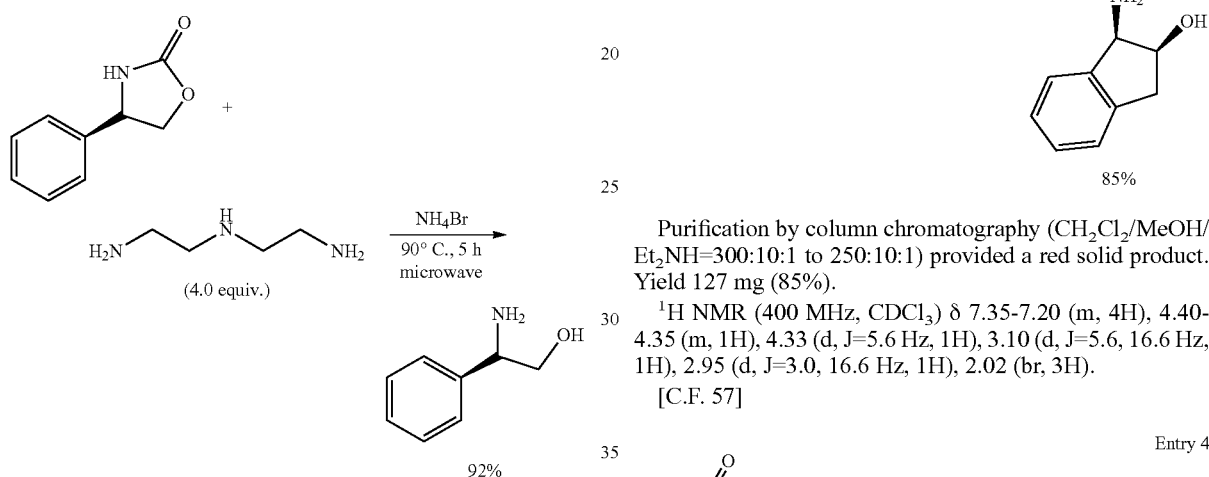

92%

The reaction was carried out at 90° C. for 5 hours under microwave irradiation conditions followed by column chromatography purification (CH$_2$Cl$_2$/MeOH/Et$_2$NH=200:10:1) to obtain a yellow solid product. Yield 126 mg (92%).

$^1$H NMR (400 MHz, CDCl$_3$) δ 7.38-7.24 (m, 5H), 4.05 (dd, J=4.4, 8.4 Hz, 1H), 3.74 (dd, J=4.4, 10.8 Hz, 1H), 3.56 (dd, J=8.4, 10.8 Hz, 1H).

[C.F.]

(3y041)

Entry 2

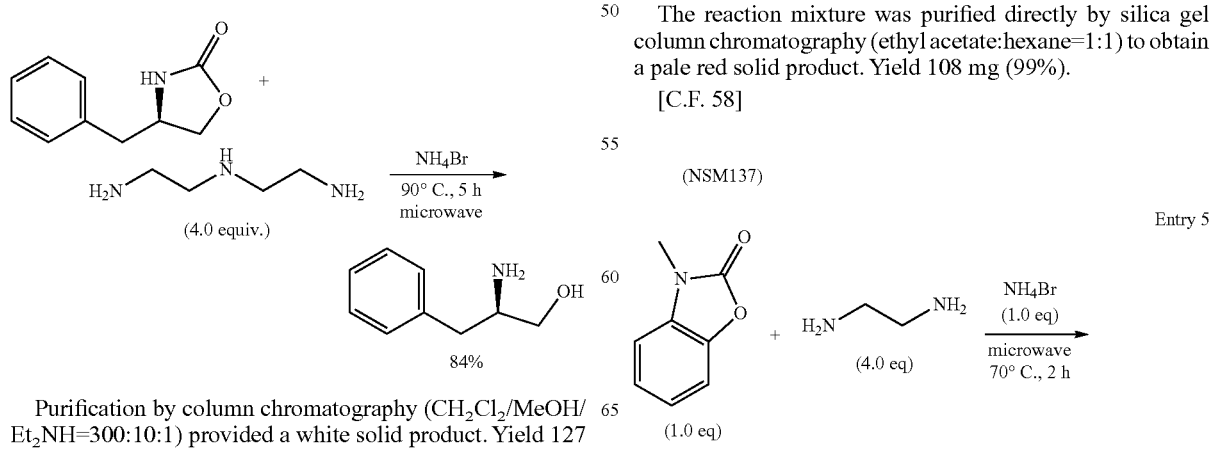

84%

Purification by column chromatography (CH$_2$Cl$_2$/MeOH/Et$_2$NH=300:10:1) provided a white solid product. Yield 127 mg (84%).

[C.F. 56]

(3y040)

Entry 3

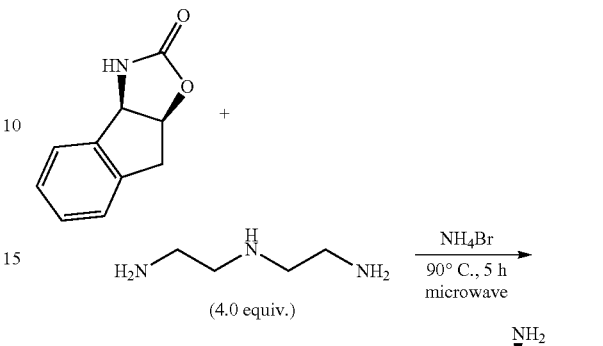

85%

Purification by column chromatography (CH$_2$Cl$_2$/MeOH/Et$_2$NH=300:10:1 to 250:10:1) provided a red solid product. Yield 127 mg (85%).

$^1$H NMR (400 MHz, CDCl$_3$) δ 7.35-7.20 (m, 4H), 4.40-4.35 (m, 1H), 4.33 (d, J=5.6 Hz, 1H), 3.10 (d, J=5.6, 16.6 Hz, 1H), 2.95 (d, J=3.0, 16.6 Hz, 1H), 2.02 (br, 3H).

[C.F. 57]

Entry 4

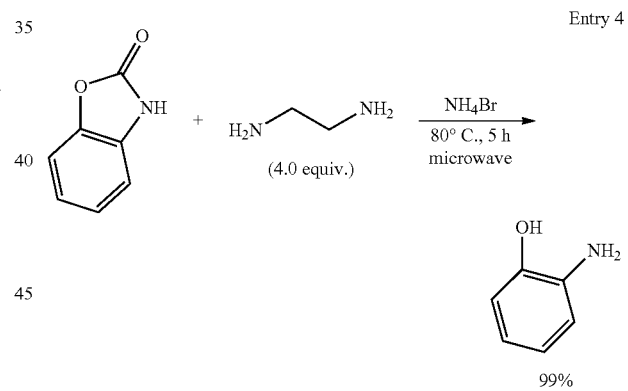

99%

The reaction mixture was purified directly by silica gel column chromatography (ethyl acetate:hexane=1:1) to obtain a pale red solid product. Yield 108 mg (99%).

[C.F. 58]

(NSM137)

Entry 5

-continued

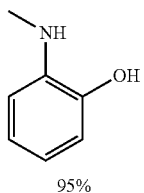

95%

A high reactivity was observed as compared with N-non-substituted reactant. Column chromatography (hexane/EtOAc=2/1 to 1/1) provided a pale pink solid product. Yield 117 mg (95%).

$^1$H NMR (400 MHz, CDCl$_3$) δ 7.00-6.85 (m, 1H), 6.80-6.55 (m, 3H), 2.87 (s, 3H).

[C.F. 59]

(3y005)

Entry 6

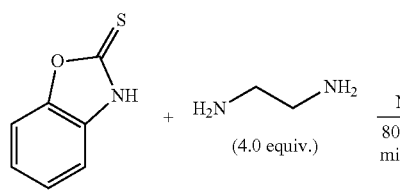

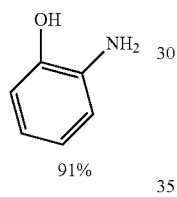

91%

The reaction mixture was purified by column chromatography (hexane/EtOAc=1/1 to ½), followed by removal of the solvent by rotary evaporation to obtain a white solid product. Yield 100 mg (91%).

$^1$H NMR (400 MHz, DMSO-d$_6$) δ 8.87 (br, 1H), 6.62 (dd, J=1.2, 7.4 Hz, 1H), 6.57 (dd, J=2.0, 7.4 Hz, 1H), 6.52 (ddd, J=1.2, 7.4, 7.4 Hz, 1H), 6.38 (ddd, J=2.0, 7.4, 7.4 Hz, 1H), 4.43 (br, 2H).

[C.F. 60]

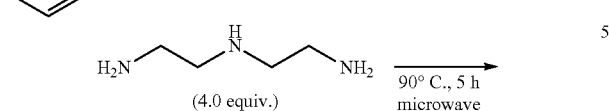

87%

The reaction was carried out in the absence of ammonium salt. The reaction mixture was purified by column chroma-tography with CH$_2$Cl$_2$/MeOH/Et$_2$NH (300:10:1) to obtain a pale yellow product. Yield 119 mg (87%).

[C.F. 61]

Entry 7

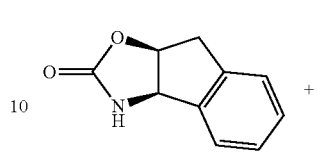

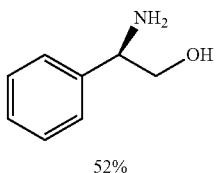

>99% (NMR)

After termination of the reaction, the reaction mixture was analyzed directly by $^1$H NMR spectroscopy in which the yield was calculated on the integrated intensity ratio of the starting materials and the product in $^1$H NMR spectrum. Yield more than 99%.

[C.F. 62]

Studies on types of amines.

Entry 8

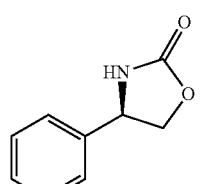

52%

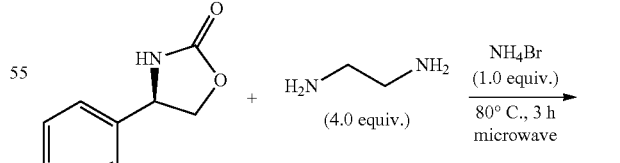

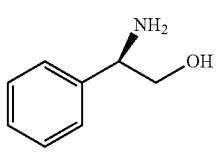

38%

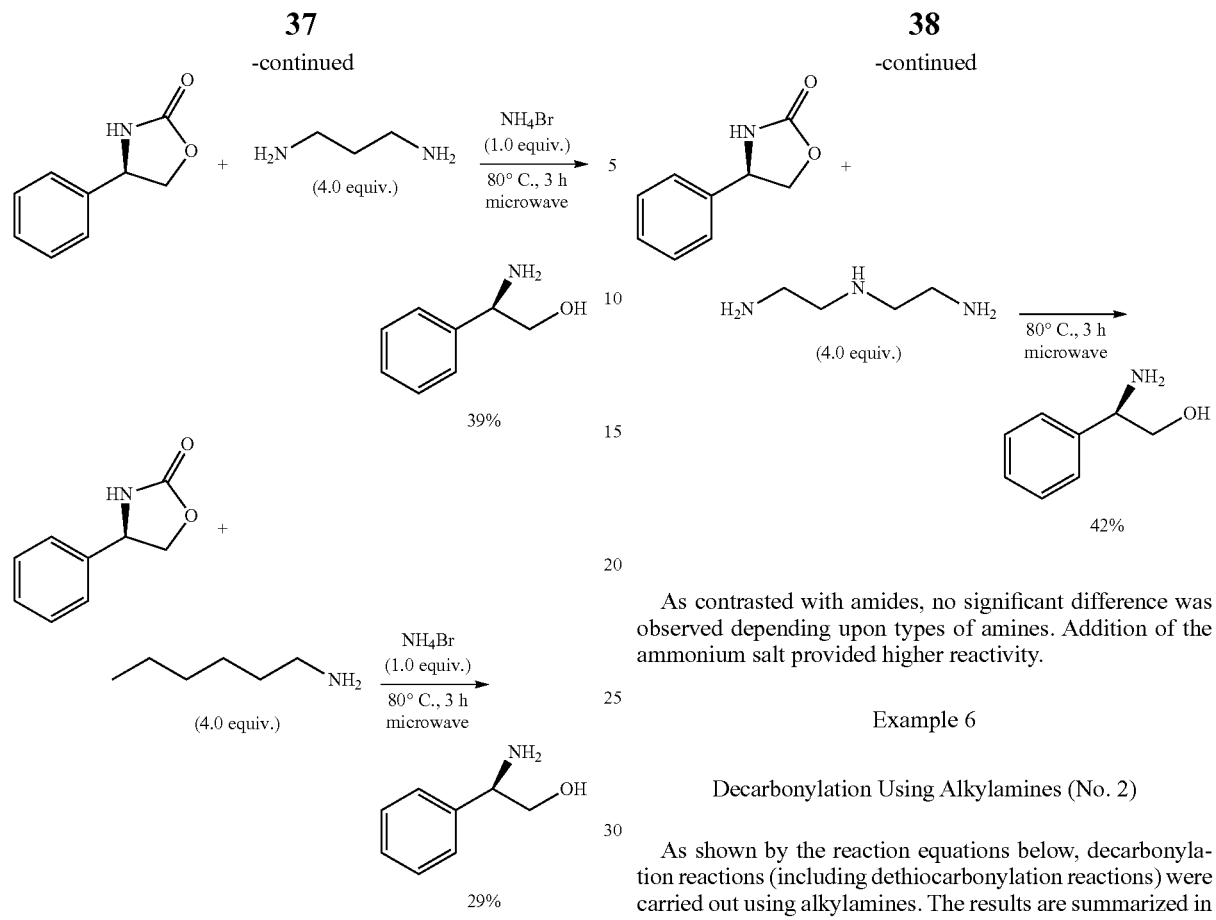

As contrasted with amides, no significant difference was observed depending upon types of amines. Addition of the ammonium salt provided higher reactivity.

Example 6

Decarbonylation Using Alkylamines (No. 2)

As shown by the reaction equations below, decarbonylation reactions (including dethiocarbonylation reactions) were carried out using alkylamines. The results are summarized in Table 8.

TABLE 8

| Entry | Substrate | Temp. [°C.] | Time [h] | Yield [%][a] |
|---|---|---|---|---|
| 1[b] | 3y013 | 80 | 5 | >95[c] |
| 2[b] | 3y144 | 80 | 5 | >95[c] |
| 3[b] | 4y031 | 80 | 5 | 85 |

TABLE 8-continued
| Entry | Substrate | Temp. [° C.] | Time [h] | Yield [%][a] |
|---|---|---|---|---|
| 4 | 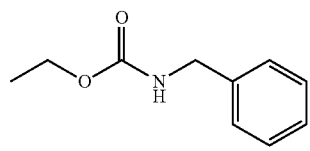<br>3y057 | 110 | 5 | >95[c] |
| 5 | 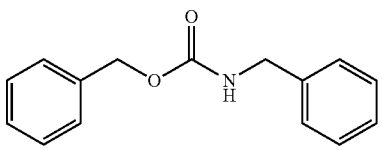 [SMILES: O=C(NCc1ccccc1)OCc1ccccc1]<br>4y019 | 100 | 5 | 84 (BnOH)<br>73[d] (BnNH$_2$) |
| 6[b] | 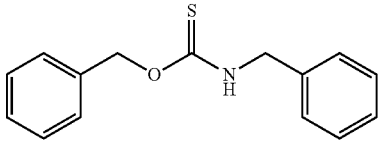 [SMILES: S=C(NCc1ccccc1)OCc1ccccc1]<br>NSM143 | 100 | 5 | 98[d] (BnNH$_2$) |
| 7[b] | 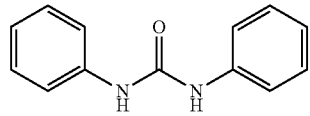 [SMILES: O=C(Nc1ccccc1)Nc1ccccc1]<br>4y018 | 80 | 5 | 76[d] |
| 8 | 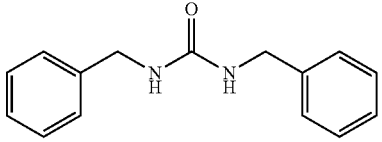 [SMILES: O=C(NCc1ccccc1)NCc1ccccc1]<br>NSM108 | 110 | 5 | >95[c] |
| 9[b] | 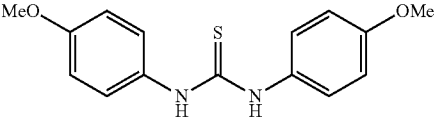 [SMILES: COc1ccc(NC(=S)Nc2ccc(OC)cc2)cc1]<br>4y016 | 80 | 5 | 94 |
| 10 | 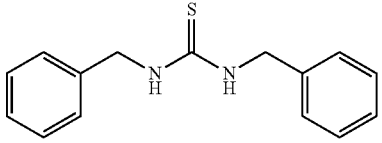 [SMILES: S=C(NCc1ccccc1)NCc1ccccc1]<br>NSM135 | 100 | 5 | 81[d] |
[a] Isolation Yield.
[b] Ethylene diamine was used.
[c] Yield was determined by $^1$H NMR analysis.
[d] Product was isolated as hydrochloride.

[C.F. 63]

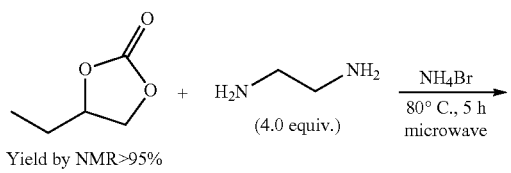

Yield by NMR>95%

[C.F. 64]

(3y144)

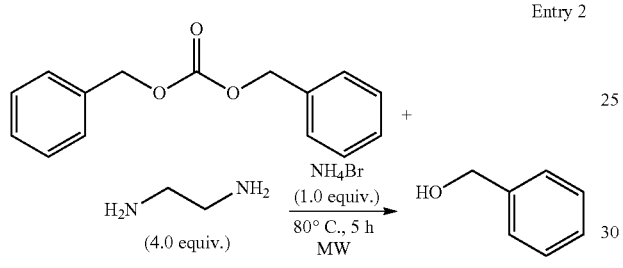

>95%

The reaction proceeded without problems even with respect to the chain carbonate.

[C.F. 65]

(4y031)

Entry 3

After termination of the reaction, the reaction mixture was purified directly by column chromatography (hexane/EtOAc=2/1). The solvent was removed by rotary evaporation to obtain a white solid product. Yield 212 mg (85%).

[C.F. 66]

(3y057)

Entry 4

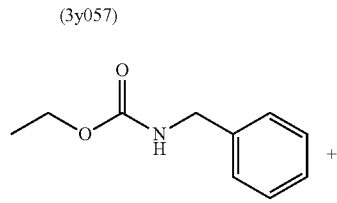

Entry 1

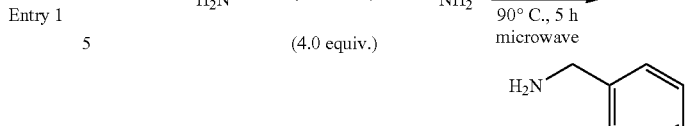

-continued

>90%

>95%

[C.F. 67]

(4y019)

Entry 5

After termination of the reaction, the reaction mixture was subjected to separation with separatory funnel with HCl aqueous solution and dichloromethane to obtain a colorless and transparent liquid product (BnOH, 91 mg, 84%). BnNH$_2$ was back-extracted from the aqueous layer. The target amine was obtained as a hydrochloride salt (104 mg, 73%).

[C.F. 68]

(NSM143)

Entry 6

1.0 eq

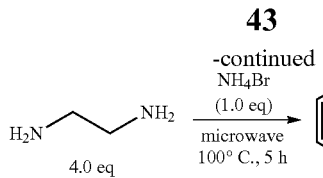

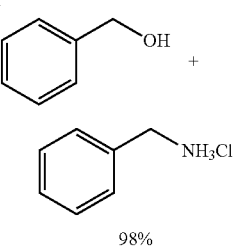

The liquid product was subjected to separation with separatory funnel with HCl aqueous solution and DCM, and then basified by adding aqueous NaOH solution to the water layer, followed by back-extraction with ether. To the resultant ether solution was added 1M HCl in Et$_2$O (5 mL), followed by stirring, filtration and washing with ether to obtain a white solid product. Yield 141 mg (98%).

$^1$H-NMR (400 MHz, DMSO-d$_6$) δ 8.29 (br, 3H), 7.50-7.28 (m, 5H), 4.02 (q, J=5.4 Hz, 2H).

[C.F. 69]

(4y018)

Entry 7

The reaction product was subjected to separation with separatory funnel with NaHCO$_3$ aqueous solution and ether, followed by addition of HCl in ether to isolate the product as a hydrochloride salt. Yield 198 mg (76%).

[C.F. 70]

(NSM108)

Entry 8

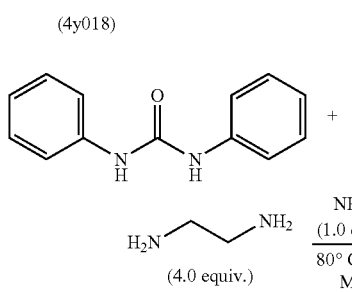

It is evidenced that the reaction can be performed even with a less reactive chain urea. Yield determined by $^1$H NMR analysis was more than 95%.

[C.F. 71]

(4y016)

Entry 9

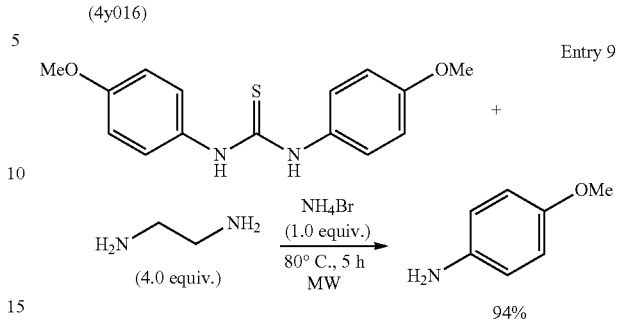

The reaction with a thiourea was studied. The product was purified by column chromatography with dichloromethane as the solvent to obtain a white solid. Yield 232 mg (94%).

[C.F. 72]

(NSM135)

Entry 10

The liquid reaction product was subjected to separation with separatory funnel with HCl aqueous solution and DCM. NaOH aqueous solution was added to the aqueous layer for basification, followed by back-extraction with ether. To the resultant ether solution was added 1 M HCl in Et$_2$O, followed by stirring, filtration and washing with ether to obtain a white solid product. Yield 233 mg (81%).

$^1$H-NMR (400 MHz, DMSO-d$_6$) δ 8.13 (br, 3H), 7.49-7.36 (m, 5H), 4.02 (s, 2H).

The invention claimed is:

1. A method for producing a first compound having at least one of an amino group and a hydroxyl group from a substrate compound having an atomic group containing a carbonyl or thiocarbonyl group CX, wherein X represents an oxygen atom or a sulfur atom, the method comprising allowing said substrate compound to react with a second compound in the presence of an ammonium salt at a temperature of 120° C. or lower to eliminate said atomic group containing the CX from said substrate compound, said second compound being expressed by formula (I):

H$_2$N-A-NH$_2$     (I)

wherein A represents:
a bond; or
an unsubstituted alkylene group having 1 to 6 carbon atoms; or a substituted alkylene group, in which one or two of the carbon atoms of an unsubstituted alkylene group having 2 to 6 carbon atoms is each substituted with a nitrogen atom.

2. The method as claimed in claim 1, wherein the ammonium salt is an ammonium halide.

3. The method as claimed in claim 2, wherein the substrate compound is an amide, the atomic group containing CX is an N-acyl group, and the reaction is carried out by eliminating the acyl group to produce the first compound from said substrate compound, the first compound having the amino group.

4. The method as claimed in claim 3, wherein the second compound is hydrazine.

5. The method as claimed in claim 3, wherein the second compound is an alkylenediamine.

6. The method as claimed in claim 5, wherein the alkylenediamine is ethylenediamine.

7. The method as claimed in claim 1, wherein the substrate compound is a cyclic carbamate, a chain carbamate, a cyclic carbonate, a chain carbonate, a cyclic urea or a chain urea, the atomic group containing CX is a carbonyl group, and the reaction of the substrate compound with an alkylenediamine as the second compound eliminates the carbonyl group to produce the first compound.

8. The method as claimed in claim 1, wherein the substrate compound is a cyclic thiocarbamate, a chain thiocarbamate, a cyclic thiocarbonate, a chain thiocarbonate, a cyclic thiourea or a chain thiourea, the atomic group containing CX is a thiocarbonyl group, and the reaction of the substrate compound with an alkylenediamine as the second compound eliminates the thiocarbonyl group to produce the first compound.

9. The method as claimed in claim 7 wherein the alkylenediamine is ethylenediamine.

10. The method as claimed in claim 1, wherein the reaction is carried out in the absence of solvent.

11. The method as claimed in claim 1, wherein the reaction is carried out under microwave irradiation.

12. The method as claimed in claim 1, wherein the first compound has an amino group.

13. The method as claimed in claim 12, wherein the first compound also has a hydroxyl group.

14. A method, for producing a first compound having at least one of an amino group and a hydroxyl group from a substrate compound having an atomic group containing a carbonyl or thiocarbonyl group CX, wherein X represents an oxygen atom or a sulfur atom, the method comprising allowing said substrate compound to react with a second compound in the presence of an ammonium salt at a temperature of 120° C. or lower to eliminate said atomic group containing the CX from said substrate compound, wherein the second compound is selected from:

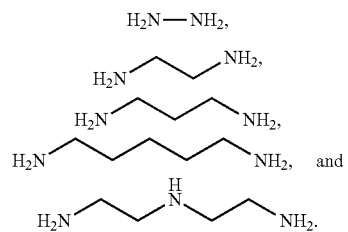

* * * * *